United States Patent
Marsh et al.

(10) Patent No.: US 10,285,928 B2
(45) Date of Patent: May 14, 2019

(54) FIBROUS STRUCTURES COMPRISING METATHESIZED UNSATURATED POLYOL ESTERS

(71) Applicant: The Procter & Gamble Company, Cincinnati, OH (US)

(72) Inventors: Randall Glenn Marsh, Hamilton, OH (US); Thomas James Klofta, Cincinnati, OH (US); Victor Nicholas Vega, Cincinnati, OH (US); Philip Andrew Sawin, Cincinnati, OH (US); Beth Ann Schubert, Maineville, OH (US); Luke Andrew Zannoni, West Chester, OH (US); Joseph Jay Kemper, Cincinnati, OH (US); Robert John Strife, West Chester, OH (US); Jeffrey John Scheibel, Glendale, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/237,724

(22) Filed: Aug. 16, 2016

(65) Prior Publication Data
US 2018/0008528 A1    Jan. 11, 2018

Related U.S. Application Data

(60) Provisional application No. 62/360,710, filed on Jul. 11, 2016.

(51) Int. Cl.
| | | |
|---|---|---|
| *A61K 8/92* | (2006.01) | |
| *A61K 8/02* | (2006.01) | |
| *A61K 8/67* | (2006.01) | |
| *A61Q 19/00* | (2006.01) | |
| *A61Q 19/10* | (2006.01) | |
| *C11C 3/12* | (2006.01) | |
| *A61K 8/37* | (2006.01) | |
| *C11D 3/37* | (2006.01) | |
| *C11D 17/04* | (2006.01) | |

(52) U.S. Cl.
CPC .......... *A61K 8/922* (2013.01); *A61K 8/0208* (2013.01); *A61K 8/375* (2013.01); *A61K 8/678* (2013.01); *A61Q 19/00* (2013.01); *A61Q 19/10* (2013.01); *C11C 3/12* (2013.01); *C11D 3/3757* (2013.01); *C11D 17/041* (2013.01); *C11D 17/049* (2013.01); *A61K 2800/56* (2013.01); *A61K 2800/805* (2013.01); *A61K 2800/87* (2013.01)

(58) Field of Classification Search
CPC ...................................................... A61K 8/922
See application file for complete search history.

(56) References Cited

U.S. PATENT DOCUMENTS

| | | |
|---|---|---|
| 2,826,551 A | 3/1958 | Geen |
| 3,964,500 A | 6/1976 | Drakoff |
| 4,152,416 A | 5/1979 | Marra et al. |
| 4,364,837 A | 12/1982 | Pader |
| 5,104,646 A | 4/1992 | Bolich et al. |
| 5,106,609 A | 4/1992 | Bolich et al. |
| 5,143,679 A | 9/1992 | Weber et al. |
| RE34,584 E | 4/1994 | Grote et al. |
| 5,518,801 A | 5/1996 | Chappell et al. |
| 5,628,097 A | 5/1997 | Curro et al. |
| 5,658,639 A | 8/1997 | Curro et al. |
| 5,879,584 A | 3/1999 | Bianchetti et al. |
| 5,914,084 A | 6/1999 | Benson et al. |
| 5,916,661 A | 6/1999 | Curro et al. |
| 6,114,263 A | 9/2000 | Benson et al. |
| 6,129,801 A | 10/2000 | Benson et al. |
| 6,383,431 B1 | 5/2002 | Dobrin et al. |
| 7,365,030 B2 | 4/2008 | Chamba et al. |
| 8,642,824 B2 | 2/2014 | Lemke et al. |
| 8,692,006 B2 | 4/2014 | Uptain et al. |
| 2003/0028165 A1 | 2/2003 | Curro et al. |
| 2004/0131820 A1 | 7/2004 | Curro et al. |
| 2004/0265534 A1 | 12/2004 | Curro et al. |
| 2005/0008680 A1 | 1/2005 | Deckner et al. |
| 2005/0008681 A1 | 1/2005 | Deckner et al. |
| 2009/0220443 A1* | 9/2009 | Braksmayer ......... A23D 7/0053 424/64 |
| 2010/0145086 A1 | 6/2010 | Schrodi et al. |
| 2011/0244199 A1 | 10/2011 | Brennan et al. |
| 2013/0344012 A1 | 12/2013 | Cohen et al. |
| 2014/0357714 A1 | 12/2014 | Braksmayer et al. |
| 2015/0017218 A1 | 1/2015 | Pettigrew et al. |
| 2015/0086659 A1 | 3/2015 | Klofta et al. |
| 2016/0089314 A1 | 3/2016 | Marsh |

FOREIGN PATENT DOCUMENTS

| | | | |
|---|---|---|---|
| GB | 849433 | 9/1960 | |
| WO | WO 2009/020665 | 2/2009 | |
| WO | WO 2009/020667 | 2/2009 | |
| WO | WO 2014133380 A1 * | 9/2014 | ............ C07C 67/08 |

OTHER PUBLICATIONS

International Search Report, PCT/US2016/047145, dated Mar. 22, 2017, 12 pages.

* cited by examiner

*Primary Examiner* — Benjamin J Packard
(74) *Attorney, Agent, or Firm* — Kathleen Y. Carter; Andrew J. Hagerty

(57) ABSTRACT

A composition comprising a metathesized polyol ester that may be combined with a fibrous structure, including a wipe.

13 Claims, No Drawings

FIBROUS STRUCTURES COMPRISING METATHESIZED UNSATURATED POLYOL ESTERS

FIELD

The present disclosure generally relates to a composition that may be incorporated into a fibrous structure for improving the perceived softness characteristics of the fibrous structure.

BACKGROUND

Fibrous structures, including wet wipes, may be useful for cleaning hard and soft surfaces. Wipes, as well as other fibrous structures, like absorbent article topsheets, may also be useful for delivering functional materials to a surface such as skin. For example, wipes and topsheets may deliver compositions that provide skin benefits, such as softening and/or moisturizing the skin, or protection from or treatment of diaper rash and other skin ailments such as eczema. The compositions delivered from the fibrous structure may also protect the skin from irritants present in certain bodily fluids like urine and bowel movements. Fibrous structures may comprise a nonwoven material, and a composition, which may be liquid. The liquid composition may be predominately aqueous, in which the components are freely soluble or where those more lipophilic components are stably dispersed or emulsified within the water. Here, the deposition of high concentrations of lipophilic ingredients can be beneficial to a surface such as skin. The liquid composition may be suitable for use on a variety of surfaces, including, for example, skin, wood, or countertops. For fibrous structures used on skin, like wipes and topsheets, the composition may comprise oligomers derived from the metathesis of unsaturated polyol esters, emulsifiers, emollients, pH adjusting agents and/or pH buffering systems, preservatives, clay minerals, rheology modifiers, and perfumes.

Some compositions for fibrous structures may comprise an emollient. The emollient may maintain or improve the health of skin by delivering beneficial components to the skin, such as an omega-3, omega-6, omega-9 and other fatty acids which make up some vegetable oil triglycerides. Some lipophilic emollients can also leave behind a protection layer on the skin to inhibit the irritation caused by urine, bowel movements, and some environmental pollutants. However, adding an emollient can be cost prohibitive and can destabilize the composition.

In order to provide skin softening benefits in a composition, a wide variety of skin emollients are used today. However, as mentioned above, the inclusion of active levels of skin softening emollients in the compositions may result in rheology and stability issues, creating consumer trade-offs in skin softening and stability of the composition used with the fibrous structure. Regarding stability, many of the unsaturated emollients used today are prone to oxidation, which can lead to consumer negatives related to off odors and decreased softness performance. This instability can require the inclusion of expensive anti-oxidants to inhibit the degradation of the composition. Further, the rising costs of some emollients, including silicones and functionalized silicones, have perpetuated the need for lower cost alternatives derived from sustainable sources.

Based on the foregoing, there is a need for new skin softening emollients that can provide softening benefits to the skin and other surfaces and can replace or be used in combination with existing emollients, such as silicone and silicone derivatives, to maximize the softening performance of the compositions. Additionally, there is a desire to find a softening active that can be derived from a sustainable source. There is also a desire to find a softening active that leads to a stable product comprising an emulsifier system.

SUMMARY

A wet wipe comprising a composition, said composition comprising;
  a) a metathesized unsaturated polyol ester, said metathesized unsaturated polyol ester having one or more of the following properties:
    (i) a weight average molecular weight of from about 5,000 Daltons to about 50,000 Daltons;
    (ii) an oligomer index from greater than 0 to 1;
    (iii) an iodine value of from about 30 to about 200;
  b) a material selected from the group consisting of emollients, clay minerals, rheology modifiers, emulsifiers, pH adjusting agents and pH buffering systems, preservatives, perfumes, and combinations thereof; and
  c) water.

These wet wipes compositions may be applied to a fibrous structure, including a co-formed fibrous structure such as a wet wipe or a baby wipe.

DETAILED DESCRIPTION

The following definitions may be useful in understanding the present disclosure.

"Loading" refers to a process of applying a liquid composition to a fibrous structure to form a wet wipe. A "loaded" fibrous structure is associated with a liquid composition.

"Soil" refers herein to matter that is extraneous to a surface being cleaned. For example, soils include body exudates, household matter, and outdoor matter. Body exudates include feces, bowel movements, menses, urine, vomitus, mucus, combinations thereof, and the like. Household matter includes food, beverages, paint, crayons, cosmetic body make-up, combinations thereof, and the like. Outdoor matter includes dirt, mud, snow, combinations thereof, and the like.

"Q.S." refers herein to "quantum sufficit" and is a sufficient percentage of water added to the composition to bring the overall composition to 100%.

Values disclosed herein as ends of ranges are not to be understood as being strictly limited to the exact numerical values recited. Instead, unless otherwise specified, each numerical range is intended to mean both the recited values and any integers within the range. For example a range disclosed as "1 to 10" is intended to mean "1, 2, 3, 4, 5, 6, 7, 8, 9, and 10".

As used herein, the articles "a" and "an" when used herein, for example, "an anionic emulsifier" or "a fiber" is understood to mean one or more of the material that is claimed or described.

"Machine direction" (MD) is used herein to refer to the direction of material flow through a process for making a fibrous structure. In addition, relative placement and movement of material can be described as flowing in the machine direction through a process from upstream in the process to downstream in the process. "Cross direction" (CD) is used herein to refer to a direction that is not parallel with, and usually perpendicular to, the machine direction.

The terms "natural oils," "natural feedstocks," or "natural oil feedstocks" may refer to oils derived from plants or animal sources. The term "natural oil" includes natural oil derivatives, unless otherwise indicated. The terms also include modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, pennycress oil, camelina oil, and castor oil. Representative non-limiting examples of animal fats include lard, tallow, poultry fat, yellow grease, and fish oil. Tall oils are by-products of wood pulp manufacture.

The term "natural oil derivatives" refers to derivatives thereof derived from natural oil. The methods used to form these natural oil derivatives may include one or more of addition, neutralization, overbasing, saponification, transesterification, esterification, amidification, hydrogenation, isomerization, oxidation, alkylation, acylation, sulfurization, sulfonation, rearrangement, reduction, fermentation, pyrolysis, hydrolysis, liquefaction, anaerobic digestion, hydrothermal processing, gasification or a combination of two or more thereof. Examples of natural derivatives thereof may include carboxylic acids, gums, phospholipids, soapstock, acidulated soapstock, distillate or distillate sludge, fatty acids, fatty acid esters, as well as hydroxy substituted variations thereof, including unsaturated polyol esters. In some embodiments, the natural oil derivative may comprise an unsaturated carboxylic acid having from about 5 to about 30 carbon atoms, having one or more carbon-carbon double bonds in the hydrocarbon (alkene) chain. The natural oil derivative may also comprise an unsaturated fatty acid alkyl (e.g., methyl) ester derived from a glyceride of natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (i.e., RBD soybean oil).

The term "free hydrocarbon" refers to any one or combination of unsaturated or saturated straight, branched, or cyclic hydrocarbons in the $C_2$ to $C_{22}$ range.

The term "metathesis monomer" refers to a single entity that is the product of a metathesis reaction which comprises a molecule of a compound with one or more carbon-carbon double bonds which has undergone an alkylidene unit interchange via one or more of the carbon-carbon double bonds either within the same molecule (intramolecular metathesis) and/or with a molecule of another compound containing one or more carbon-carbon double bonds such as an olefin (intermolecular metathesis).

The term "metathesis dimer" refers to the product of a metathesis reaction wherein two reactant compounds, which can be the same or different and each with one or more carbon-carbon double bonds, are bonded together via one or more of the carbon-carbon double bonds in each of the reactant compounds as a result of the metathesis reaction.

The term "metathesis trimer" refers to the product of one or more metathesis reactions wherein three molecules of two or more reactant compounds, which can be the same or different and each with one or more carbon-carbon double bonds, are bonded together via one or more of the carbon-carbon double bonds in each of the reactant compounds as a result of the one or more metathesis reactions, the trimer containing three bonded groups derived from the reactant compounds.

The term "metathesis tetramer" refers to the product of one or more metathesis reactions wherein four molecules of two or more reactant compounds, which can be the same or different and each with one or more carbon-carbon double bonds, are bonded together via one or more of the carbon-carbon double bonds in each of the reactant compounds as a result of the one or more metathesis reactions, the tetramer containing four bonded groups derived from the reactant compounds.

The term "metathesis pentamer" refers to the product of one or more metathesis reactions wherein five molecules of two or more reactant compounds, which can be the same or different and each with one or more carbon-carbon double bonds, are bonded together via one or more of the carbon-carbon double bonds in each of the reactant compounds as a result of the one or more metathesis reactions, the pentamer containing five bonded groups derived from the reactant compounds.

The term "metathesis hexamer" refers to the product of one or more metathesis reactions wherein six molecules of two or more reactant compounds, which can be the same or different and each with one or more carbon-carbon double bonds, are bonded together via one or more of the carbon-carbon double bonds in each of the reactant compounds as a result of the one or more metathesis reactions, the hexamer containing six bonded groups derived from the reactant compounds.

The term "metathesis heptamer" refers to the product of one or more metathesis reactions wherein seven molecules of two or more reactant compounds, which can be the same or different and each with one or more carbon-carbon double bonds, are bonded together via one or more of the carbon-carbon double bonds in each of the reactant compounds as a result of the one or more metathesis reactions, the heptamer containing seven bonded groups derived from the reactant compounds.

The term "metathesis octamer" refers to the product of one or more metathesis reactions wherein eight molecules of two or more reactant compounds, which can be the same or different and each with one or more carbon-carbon double bonds, are bonded together via one or more of the carbon-carbon double bonds in each of the reactant compounds as a result of the one or more metathesis reactions, the octamer containing eight bonded groups derived from the reactant compounds.

The term "metathesis nonamer" refers to the product of one or more metathesis reactions wherein nine molecules of two or more reactant compounds, which can be the same or different and each with one or more carbon-carbon double bonds, are bonded together via one or more of the carbon-carbon double bonds in each of the reactant compounds as a result of the one or more metathesis reactions, the nonamer containing nine bonded groups derived from the reactant compounds.

The term "metathesis decamer" refers to the product of one or more metathesis reactions wherein ten molecules of two or more reactant compounds, which can be the same or different and each with one or more carbon-carbon double bonds, are bonded together via one or more of the carbon-carbon double bonds in each of the reactant compounds as a result of the one or more metathesis reactions, the decamer containing ten bonded groups derived from the reactant compounds.

The term "metathesis oligomer" refers to the product of one or more metathesis reactions wherein two or more molecules (e.g., 2 to about 10, or 2 to about 4) of two or more reactant compounds, which can be the same or different and each with one or more carbon-carbon double bonds, are bonded together via one or more of the carbon-carbon double bonds in each of the reactant compounds as a result of the one or more metathesis reactions, the oligomer containing a few (e.g., 2 to about 10, or 2 to about 4) bonded groups derived from the reactant compounds. In some embodiments, the term "metathesis oligomer" may include metathesis reactions wherein greater than ten molecules of two or more reactant compounds, which can be the same or different and each with one or more carbon-carbon double bonds, are bonded together via one or more of the carbon-carbon double bonds in each of the reactant compounds as a result of the one or more metathesis reactions, the oligomer containing greater than ten bonded groups derived from the reactant compounds.

As used herein, the term "polyol" means an organic material comprising at least two hydroxy moieties.

All percentages and ratios are calculated by weight unless otherwise indicated. All percentages and ratios are calculated based on the total composition unless otherwise indicated.

Unless otherwise noted, all component or composition levels are in reference to the active level of that component or composition, and are exclusive of impurities, for example, residual solvents or by-products, which may be present in commercially available sources. The present disclosure includes wet wipes, and, more particularly, includes wet wipes comprising a fibrous structure in combination with a liquid composition. The liquid composition may be aqueous.

The liquid compositions may comprise an emollient. A liquid composition comprising an emollient may be useful for improving and/or maintaining skin health. In particular, a liquid composition comprising an emollient may deliver beneficial compounds, such as essential fatty acids, to the skin. In addition, the emollient may soothe, soften, protect, moisturize, heal, or otherwise improve the condition and/or appearance and/or the softness of the skin. Furthermore, natural emollients may be selected, which may appeal to users who are concerned about the health effects of synthetic compounds. However, incorporating an emollient into an aqueous liquid composition can be difficult. Moreover, incorporating an emollient into an aqueous composition may have negative tactile sensation for some consumers, as the liquid composition may feel too greasy, slippery, sticky, and/or slimy.

Liquid compositions of the present disclosure may comprise a clay mineral. It has been found that a liquid composition comprising a level of emollient sufficient to deliver beneficial compounds to the skin in combination with a clay mineral has little to no greasy, slippery, and/or slimy feel. Without wishing to be bound by theory, it is believed that a clay mineral reduces the greasy, slippery, and/or slimy feel of the emollient by introducing a more powdery feel that works in synergy with the emollient to make a more preferred tactile sensory experience for users. Moreover, a liquid composition comprising an emollient and a clay mineral has acceptable stability for use in a wet wipe. Additionally, it has been found that a liquid composition comprising an emollient, a clay mineral, and a rheology modifier may further reduce the greasy, slippery, sticky and/or slimy feel of the emollient to produce a more preferred tactile sensory experience for caregivers, while minimizing the amount of clay mineral that is needed in the liquid composition.

Liquid compositions of the present disclosure may comprise a rheology modifier. The liquid composition may comprise one or more rheology modifiers. A rheology modifier may (1) help to stabilize the liquid composition on a fibrous structure and reduce settling of the liquid to the bottom of a package, (2) help stabilize the liquid emulsion composition by reducing the probability for phase separation, (3) enhance the transfer of the liquid composition to the skin, and (4) enhance the uniformity of the layer of the liquid composition on the skin by reducing the probability of phase separation in the liquid composition. For example, rheology modifiers may help to preserve a homogeneous distribution of the liquid composition within a stack of the fibrous structures. Any composition that is in fluid form may have a tendency to migrate to the lower part of the wipes stack during prolonged storage. This effect may create an upper part of the stack of fibrous structures having less liquid composition than the bottom part of the stack.

Without wishing to be bound by theory, it is believed that rheology modifiers may enhance the liquid composition comprising an emollient and a clay mineral. The rheology modifier may minimize the greasy and/or slimy feel of a liquid composition comprising an emollient. Without wishing to be bound by theory, it is believed that the clay mineral is wetting both the lipophilic emollient droplets and the hydrophilic aqueous phase of the liquid composition. In doing so, the clay mineral forms a barrier to prevent emollient droplets from coalescing such that the emulsion stability is enhanced. Additionally, it is believed that the clay mineral reduces the greasy feel such that the tactile sensory characteristics of the liquid composition become more powdery and lighter in feel.

Liquid compositions of the present disclosure may comprise an emulsifier. The emulsifier may stabilize the incorporation of lipophilic emollients to the water phase of the liquid composition. The emulsifier may aid in dissolution and removal of the soils from the surface being cleansed. The emulsifier or combinations of emulsifiers may be mild, which means that the emulsifiers provide sufficient cleaning or detersive benefits but do not overly dry or otherwise harm or damage the skin.

Liquid compositions of the present disclosure may comprise a preservative. The liquid composition may comprise a preservative or a combination of preservatives acting together as a preservative system. Preservatives and preservative systems are used interchangeably in the present disclosure to indicate one unique or a combination of preservative compounds. A preservative may be understood to be a chemical or natural compound or a combination of compounds reducing the growth of microorganisms, thus enabling a longer shelf life for a package of fibrous structures (opened or not opened) as well as creating an environment with reduced growth of microorganisms when transferred to the skin during the wiping process.

The composition of the present disclosure may be incorporated onto a fibrous structure substrate at a load of about 200% to about 600% by weight of the substrate. In some exemplary configurations, a wet wipe comprising a substrate may comprise or be impregnated with the lotion emulsion composition with a lotion load of about 325% to 460%.

Wet wipes of the present disclosure may have different properties on different sides of the wet wipe. For example, one side of the wipe may have good cleaning performance and the other side of the wet wipe may have good tactile sensation to the user. In another example, one side of the wet wipe may have an increased cleaning performance as compared to the other side of the wet wipe.

While the present disclosure references the use of a wet wipe for cleaning skin, it is to be appreciated that the wet wipes of the present disclosure may be used to clean various other surfaces other than skin, including countertops, walls, floors, appliances, furniture, and the like.

Fibrous Structures

"Fibrous structure" as used herein means a structure that comprises one or more filaments and/or fibers. In one example, the fibrous structure is a wipe, such as a wet wipe, for example a baby wipe. For example, "fibrous structure" and "wipe" may be used interchangeably herein. In one example, a fibrous structure according to the present disclosure means an orderly arrangement of filaments and/or fibers within a structure in order to perform a function. In another example, a fibrous structure according to the present disclosure is a nonwoven.

Non-limiting examples of processes for making fibrous structures include known wet-laid papermaking processes, air-laid papermaking processes including carded and/or spunlaced processes. Such processes typically include steps of preparing a fiber composition in the form of a suspension in a medium, either wet, more specifically aqueous medium, or dry, more specifically gaseous, i.e. with air as medium. The aqueous medium used for wet-laid processes is oftentimes referred to as a fiber slurry. The fibrous slurry is then used to deposit a plurality of fibers onto a forming wire or belt such that an embryonic fibrous structure is formed, after which drying and/or bonding the fibers together results in a fibrous structure. Further processing the fibrous structure may be carried out such that a finished fibrous structure is formed. For example, in typical papermaking processes, the finished fibrous structure is the fibrous structure that is wound on the reel at the end of papermaking, and may subsequently be converted into a finished product, e.g. a sanitary tissue product.

The fibrous structures of the present disclosure may be homogeneous or may be layered. If layered, the fibrous structures may comprise at least two and/or at least three and/or at least four and/or at least five layers.

In one example the fibrous structure is a nonwoven.

"Nonwoven" for purposes of the present disclosure as used herein and as defined by EDANA means a sheet of fibers, continuous filaments, or chopped yarns of any nature or origin, that have been formed into a web by any means, and bonded together by any means, with the exception of weaving or knitting. Felts obtained by wet milling are not nonwovens. Wetlaid webs are nonwovens provided that they contain a minimum of 50% by weight of man-made fibers, filaments or other fibers of non-vegetable origin with a length to diameter ratio that equals or exceeds 300 or a minimum of 30% by weight of man-made fibers, filaments or other fibers of non-vegetable origin with a length to diameter ratio that equals or exceeds 600 and a maximum apparent density of 0.40 g/cm$^3$.

The fibrous structures of the present disclosure may be co-formed fibrous structures.

"Co-formed fibrous structure" as used herein means that the fibrous structure comprises a mixture of at least two different materials wherein at least one of the materials comprises a filament, such as a polypropylene filament, and at least one other material, different from the first material, comprises a solid additive, such as a fiber and/or a particulate. In one example, a co-formed fibrous structure comprises solid additives, such as fibers, such as wood pulp fibers and/or absorbent gel materials and/or filler particles and/or particulate spot bonding powders and/or clays, and filaments, such as polypropylene filaments.

"Solid additive" as used herein means a fiber and/or a particulate.

"Particulate" as used herein means a granular substance or powder.

"Fiber" and/or "Filament" as used herein means an elongate particulate having an apparent length greatly exceeding its apparent width, i.e. a length to diameter ratio of at least about 10. For purposes of the present disclosure, a "fiber" is an elongate particulate as described above that exhibits a length of less than 5.08 cm (2 in.) and a "filament" is an elongate particulate as described above that exhibits a length of greater than or equal to 5.08 cm (2 in.).

Fibers are typically considered discontinuous in nature. Non-limiting examples of fibers include wood pulp fibers; rayon, which in turn includes but is not limited to viscose, lyocell, cotton; wool; silk; jute; linen; ramie; hemp; flax; camel hair; kenaf; and synthetic staple fibers made from polyester, nylons, polyolefins such as polypropylene, polyethylene, natural polymers, such as starch, starch derivatives, cellulose and cellulose derivatives, hemicellulose, hemicellulose derivatives, chitin, chitosan, polyisoprene (cis and trans), peptides, polyhydroxyalkanoates, copolymers of polyolefins such as polyethylene-octene, and biodegradable or compostable thermoplastic fibers such as polylactic acid filaments, polyvinyl alcohol filaments, and polycaprolactone filaments. The fibers may be monocomponent or multicomponent, such as bicomponent filaments, round, non-round fibers; and combinations thereof.

Filaments are typically considered continuous or substantially continuous in nature. Filaments are relatively longer than fibers. Non-limiting examples of filaments include meltblown and/or spunbond filaments. Non-limiting examples of materials that can be spun into filaments include natural polymers, such as starch, starch derivatives, cellulose and cellulose derivatives, hemicellulose, hemicellulose derivatives, chitin, chitosan, polyisoprene (cis and trans), peptides, polyhydroxyalkanoates, and synthetic polymers including, but not limited to, thermoplastic polymer filaments comprising thermoplastic polymers, such as polyesters, nylons, polyolefins such as polypropylene filaments, polyethylene filaments, polyvinyl alcohol and polyvinyl alcohol derivatives, sodium polyacrylate (absorbent gel material) filaments, and copolymers of polyolefins such as polyethylene-octene, and biodegradable or compostable thermoplastic fibers such as polylactic acid filaments, polyvinyl alcohol filaments, and polycaprolactone filaments. The filaments may be monocomponent or multicomponent, such as bicomponent filaments.

In one example of the present disclosure, "fiber" refers to papermaking fibers. Papermaking fibers useful in the present disclosure include cellulosic fibers commonly known as wood pulp fibers. Applicable wood pulps include chemical pulps, such as Kraft, sulfite, and sulfate pulps, as well as mechanical pulps including, for example, groundwood, thermomechanical pulp and chemically modified thermomechanical pulp. Chemical pulps, however, may be preferred since they impart a superior tactile sense of softness to tissue sheets made therefrom. Pulps derived from both deciduous trees (hereinafter, also referred to as "hardwood") and coniferous trees (hereinafter, also referred to as "softwood") may be utilized. The hardwood and softwood fibers can be blended, or alternatively, can be deposited in layers to provide a stratified web. These references disclose layering of hardwood and softwood fibers. Also applicable to the present disclosure are fibers derived from recycled paper, which may contain any or all of the above categories as well as other non-fibrous materials such as fillers and adhesives used to facilitate the original papermaking.

In addition to the various wood pulp fibers, other cellulosic fibers such as cotton linters, rayon, lyocell and bagasse can be used with the present disclosure. Other sources of cellulose in the form of fibers or capable of being spun into fibers include grasses and grain sources.

"Sanitary tissue product" as used herein means a soft, low density (i.e. <about 0.15 g/cm$^3$) web useful as a wiping implement for post-urinary and post-bowel movement cleaning (toilet tissue), for otorhinolaryngological discharges (facial tissue), and multi-functional absorbent and cleaning uses (absorbent towels). Non-limiting examples of suitable sanitary tissue products of the present disclosure include paper towels, bath tissue, facial tissue, napkins, baby wipes, adult wipes, wet wipes, cleaning wipes, polishing wipes, cosmetic wipes, car care wipes, wipes that comprise an active agent for performing a particular function, cleaning fibrous structures for use with implements, such as a SWIFFER® cleaning wipe/pad. The sanitary tissue product may be convolutely wound upon itself about a core or without a core to form a sanitary tissue product roll.

In one example, the sanitary tissue product of the present disclosure comprises a fibrous structure according to the present disclosure.

The sanitary tissue products of the present disclosure may exhibit a basis weight between about 10 g/m$^2$ to about 120 g/m$^2$ and/or from about 15 g/m$^2$ to about 110 g/m$^2$ and/or from about 20 g/m$^2$ to about 100 g/m$^2$ and/or from about 30 to 90 g/m$^2$. In addition, the sanitary tissue product of the present disclosure may exhibit a basis weight between about 40 g/m$^2$ to about 120 g/m$^2$ and/or from about 50 g/m$^2$ to about 110 g/m$^2$ and/or from about 55 g/m$^2$ to about 105 g/m$^2$ and/or from about 60 to 100 g/m$^2$.

The sanitary tissue products of the present disclosure may exhibit a density (measured at 95 g/in$^2$) of less than about 0.60 g/cm$^3$ and/or less than about 0.30 g/cm$^3$ and/or less than about 0.20 g/cm$^3$ and/or less than about 0.10 g/cm$^3$ and/or less than about 0.07 g/cm$^3$ and/or less than about 0.05 g/cm$^3$ and/or from about 0.01 g/cm$^3$ to about 0.20 g/cm$^3$ and/or from about 0.02 g/cm$^3$ to about 0.10 g/cm$^3$.

The sanitary tissue products of the present disclosure may comprises additives such as softening agents, temporary wet strength agents, permanent wet strength agents, bulk softening agents, silicones, wetting agents, latexes, especially surface-pattern-applied latexes, dry strength agents such as carboxymethylcellulose and starch, and other types of additives suitable for inclusion in and/or on sanitary tissue products.

"Weight average molecular weight" as used herein means the weight average molecular weight as determined using gel permeation chromatography according to the protocol found in Colloids and Surfaces A. Physico Chemical & Engineering Aspects, Vol. 162, 2000, pg. 107-121.

"Basis Weight" as used herein is the weight per unit area of a sample reported in lbs/3000 ft$^2$ or g/m$^2$ (gsm).

"Stack" as used herein, refers to a neat pile of fibrous structures and/or wipes. Based upon the assumption that there are at least three wipes in a stack, each wipe, except for the topmost and bottommost wipes in the stack, will be directly in face to face contact with the wipe directly above and below itself in the stack. Moreover, when viewed from above, the wipes will be layered on top of each other, or superimposed, such that only the topmost wipe of the stack will be visible. The height of the stack is measured from the bottom of the bottommost wipe in the stack to the top of the topmost wipe in the stack and is provided in units of millimeters (mm).

When present on or in the fibrous structure, the liquid composition may be present at a level of from about 10% to about 1000% of the basis weight of the fibrous structure and/or from about 100% to about 700% of the basis weight of the fibrous structure and/or from about 200% to about 500% and/or from about 200% to about 400% of the basis weight of the fibrous structure.

"Wet" refers to fibrous structures and/or wipes which are moistened with a liquid composition prior to packaging in a generally moisture impervious container or wrapper. Such wet wipes, which can also be referred to in commerce as "towelettes" or "pre-moistened wipes", may be suitable for use in cleaning babies, as well as older children and adults.

"Saturation loading" and "lotion loading" are used interchangeably herein and refer to the amount of liquid composition applied to the fibrous structure or wipe. In general, the amount of liquid composition applied may be chosen in order to provide maximum benefits to the end product comprised by the wipe. Saturation loading is typically expressed as grams of liquid composition per gram of dry wipe.

Saturation loading, often expressed as percent saturation, is defined as the percentage of the dry fibrous structure or wipe's mass (void of any liquid composition) that a liquid composition present on/in the fibrous structure or wipe represents. For example, a saturation loading of 1.0 (equivalently, 100% saturation) indicates that the mass of liquid composition present on/in the fibrous structure or wipe is equal to the mass of dry fibrous structure or wipe (void of any liquid composition).

The following equation is used to calculate saturation load of a fibrous structure or wipe:

$$\text{Saturation Loading} = \left[\frac{\text{wet wipe mass}}{(\text{wipe size}) * (\text{basis weight})}\right] - 1$$

"Saturation gradient index" (SGI) is a measure of how well the wipes at the top of a stack retain moisture. The SGI of a stack of wipes is measured as described above and is calculated as the ratio of the average lotion load of the bottommost wipes in the stack versus the topmost wipes in the stack. The ideal stack of wipes will have an SGI of about 1.0; that is, the topmost wipes will be equally as moist as the bottommost wipes. In the aforementioned exemplary configurations, the stacks have a SGI from about 1.0 to about 1.5.

The saturation gradient index for a fibrous structure or wipe stack is calculated as the ratio of the saturation loading of a set number of fibrous structures or wipes from the bottom of a stack to that of the same number of fibrous structures or wipes from the top of the stack. For example, for an approximately 80 count wipe stack, the saturation gradient index is this ratio using 10 wipes from bottom and top; for an approximately 30 count wipe stack, 5 wipes from bottom and top are used; and for less than 30, only the top and bottom single wipes are used in the saturation gradient index calculation. The saturation gradient index for a wipe stack is performed at least seven days after the wipe stack is produced. The following equation illustrates the example of an 80 count stack saturation gradient index calculation:

$$\text{Saturation Gradient Index} = \frac{\text{average lotion load of bottom 10 wipes in stack}}{\text{average lotion load of top 10 wipes in stack}}$$

A saturation profile, or wetness gradient, exists in the stack when the saturation gradient index is greater than 1.0. In cases where the saturation gradient index is significantly greater than 1.0, e.g. over about 1.5, lotion is draining from the top of the stack and settling in the bottom of the container, such that there may be a noticeable difference in the wetness of the topmost fibrous structures or wipes in the stack compared to that of the fibrous structures or wipes nearest the bottom of the stack. For example, a perfect tub of wipes would have a saturation gradient index of 1.0; the bottommost wipes and topmost wipes would maintain equivalent saturation loading during storage. Additional liquid composition would not be needed to supersaturate the wipes in an effort to keep all of the wipes moist, which typically results in the bottommost wipes being soggy.

"Percent moisture" or "% moisture" or "moisture level" as used herein means 100× (the ratio of the mass of water contained in a fibrous structure to the mass of the fibrous structure). The product of the above equation is reported as a %.

"Surface tension" as used herein, refers to the force at the interface between a liquid composition and air. Surface tension is typically expressed in dynes per centimeter (dynes/cm).

"Visible" as used herein, refers to being capable of being seen by the naked eye when viewed at a distance of 12 inches (in), or 30.48 centimeters (cm), under the unimpeded light of an ordinary incandescent 60 watt light bulb that is inserted in a fixture such as a table lamp. It follows that "visually distinct" as used herein refers to those features of nonwoven wipes, whether or not they are wet, that are readily visible and discernible when the wipe is subjected to normal use, such as the cleaning of a child's skin.

"Ply" as used herein means an individual, integral fibrous structure.

"Plies" as used herein means two or more individual, integral fibrous structures disposed in a substantially contiguous, face-to-face relationship with one another, forming a multi-ply fibrous structure and/or multi-ply sanitary tissue product. It is also contemplated that an individual, integral fibrous structure can effectively form a multi-ply fibrous structure, for example, by being folded on itself.

In yet another example, a fibrous structure of the present disclosure may comprise two outer layers consisting of 100% by weight filaments and an inner layer consisting of 100% by weight fibers.

The fibrous structures of the present disclosure may comprise any suitable amount of filaments and any suitable amount of solid additives. For example, the fibrous structures may comprise from about 10% to about 70% and/or from about 20% to about 60% and/or from about 30% to about 50% by dry weight of the fibrous structure of filaments and from about 90% to about 30% and/or from about 80% to about 40% and/or from about 70% to about 50% by dry weight of the fibrous structure of solid additives, such as wood pulp fibers. In one example, the fibrous structures of the present disclosure comprise filaments.

The filaments and solid additives of the present disclosure may be present in fibrous structures according to the present disclosure at weight ratios of filaments to solid additives of from at least about 1:1 and/or at least about 1:1.5 and/or at least about 1:2 and/or at least about 1:2.5 and/or at least about 1:3 and/or at least about 1:4 and/or at least about 1:5 and/or at least about 1:7 and/or at least about 1:10.

The fibrous structures of the present disclosure and/or any sanitary tissue products comprising such fibrous structures may be subjected to any post-processing operations such as embossing operations, printing operations, tuft-generating operations, thermal bonding operations, ultrasonic bonding operations, perforating operations, surface treatment operations such as application of lotions, silicones and/or other materials, folding, and mixtures thereof.

Non-limiting examples of suitable polypropylenes for making the filaments of the present disclosure are commercially available from Lyondell-Basell and Exxon-Mobil.

Any hydrophobic or non-hydrophilic materials within the fibrous structure, such as polypropylene filaments, may be surface treated and/or melt treated with a hydrophilic modifier. Non-limiting examples of surface treating hydrophilic modifiers include emulsifiers, such as Triton X-100. Non-limiting examples of melt treating hydrophilic modifiers that are added to the melt, such as the polypropylene melt, prior to spinning filaments, include hydrophilic modifying melt additives such as VW351 and/or S-1416 commercially available from Polyvel, Inc. and Irgasurf commercially available from Ciba. The hydrophilic modifier may be associated with the hydrophobic or non-hydrophilic material at any suitable level known in the art. In one example, the hydrophilic modifier is associated with the hydrophobic or non-hydrophilic material at a level of less than about 20% and/or less than about 15% and/or less than about 10% and/or less than about 5% and/or less than about 3% to about 0% by dry weight of the hydrophobic or non-hydrophilic material.

The fibrous structures of the present disclosure may include optional additives, each, when present, at individual levels of from about 0% and/or from about 0.01% and/or from about 0.1% and/or from about 1% and/or from about 2% to about 95% and/or to about 80% and/or to about 50% and/or to about 30% and/or to about 20% by dry weight of the fibrous structure. Non-limiting examples of optional additives include permanent wet strength agents, temporary wet strength agents, dry strength agents such as carboxymethylcellulose and/or starch, softening agents, lint reducing agents, opacity increasing agents, wetting agents, odor absorbing agents, perfumes, temperature indicating agents, color agents, dyes, osmotic materials, microbial growth detection agents, antibacterial agents and mixtures thereof. Non-limiting examples of optional melt additives include opacity increasing agents, wetting agents, odor absorbing agents, perfumes, temperature indicating agents, color agents, dyes, osmotic materials, microbial growth detection agents, antibacterial agents and mixtures thereof.

Compositions

As discussed above, a wet wipe may include a fibrous structure in combination with a liquid composition.

TABLE 1

| Liquid Compositions | |
| --- | --- |
| Comp. No. | Composition |
| 1 | A composition comprising, a) a metathesized unsaturated polyol ester, said metathesized unsaturated polyol ester having one or more of the following properties: (i) a weight average molecular weight of from about 5,000 Daltons to about 50,000 Daltons, from about 5,500 Daltons to about 50,000 Daltons, from about 5,500 Daltons to about 40,000 Daltons, or from about 6,000 Daltons to about 30,000 Daltons; |

TABLE 1-continued

Liquid Compositions

| Comp. No. | Composition |
|---|---|
| | (ii) an oligomer index from greater than 0 to 1, from 0.001 to 1, 0.01 to 1, or from 0.05 to 1;<br>(iii) an iodine value of from about 30 to about 200, from about 30 to about 150, from about 30 to about 120, or from about 50 to about 110; and<br>b) a material selected from the group consisting of emollients, clay minerals, rheology modifiers, emulsifiers, pH adjusting agents and pH buffering systems, preservatives, perfumes, and combinations thereof;<br>c) water |
| 2 | In one aspect of said composition 1 of Table 1, said metathesized unsaturated polyol ester has the weight average molecular weight property from a)(i) above. |
| 3 | In one aspect of said composition 1 of Table 1, said metathesized unsaturated polyol ester has the oligomer index property from a)(ii) above. |
| 4 | In one aspect of said composition 1 of Table 1, said metathesized unsaturated polyol ester has the iodine value property from a)(iii) above. |
| 5 | In one aspect of said composition 1 of Table 1, said metathesized unsaturated polyol ester has the property from a)(i) and from a)(ii) above. |
| 6 | In one aspect of said composition 1 of Table 1, said metathesized unsaturated polyol ester has the properties from a)(i) and from a)(iii) above. |
| 7 | In one aspect of said composition 1 of Table 1, said metathesized unsaturated polyol ester has the properties from a)(ii) and from a)(iii) above. |
| 8 | In one aspect of said composition 1 of Table 1, said metathesized unsaturated polyol ester has the properties from a)(i), a)(ii) and from a)(iii) above. |
| 9 | In one aspect, of compositions 1, 2, 3, 4, 5, 6, 7, and 8 of Table 1, said metathesized unsaturated polyol ester has a free hydrocarbon content, based on total weight of metathesized unsaturated polyol ester, of from about 0% to about 5%, from about 0.1% to about 5%, from about 0.1% to about 4%, or from about 0.1 to about 3%. |
| 10 | In one aspect of Table 1 Compositions 1, 2, 3, 4, 5, 6, 7, 8, and 9 the metathesized unsaturated polyol ester is metathesized at least once. |
| 11 | In one aspect, of compositions 1, 2, 3, 4, 5, 6, 7, 8, 9 and 10 of Table 1, said composition comprises, based on total composition weight, from about 0.01% to about 10%, from about 0.1% to about 8%, or from about 0.2% to about 4% of said metathesized unsaturated polyol ester. |

TABLE 2

Liquid Compositions

| Comp. No. | Composition |
|---|---|
| 1 | A composition comprising:<br>a) a metathesized unsaturated polyol ester, said metathesized unsaturated polyol ester having a weight average molecular weight of from about 2,000 Daltons to about 50,000 Daltons, from about 2,500 Daltons to about 50,000 Daltons, from about 3,000 Daltons to about 40,000 Daltons, from about 3,000 Daltons to about 30,000 Daltons; and one or more of the following properties:<br>(i) a free hydrocarbon content, based on total weight of metathesized unsaturated polyol ester, of from about 0% to about 5%, from about 0.1% to about 5%, from about 0.1% to about 4%, or from about 0.1 to about 3%;<br>(ii) an oligomer index from greater than 0 to 1, from 0.001 to 1, 0.01 to 1, or from 0.05 to 1;<br>(iii) an iodine value of from about 8 to about 200, from about 10 to about 200, from about 20 to about 150, from about 30 to about 120; and<br>b) a material selected from the group consisting of emollients, clay minerals, rheology modifiers, emulsifiers, pH adjusting agents and pH buffering systems, preservatives, perfumes, and combinations thereof;<br>c) water |
| 2 | In one aspect of said composition 1 of Table 2, said metathesized unsaturated polyol ester has the free hydrocarbon content property from a)(i) above. |
| 3 | In one aspect of said composition 1 of Table 2, said metathesized unsaturated polyol ester has the oligomer index property from a)(ii) above. |
| 4 | In one aspect of said composition 1 of Table 2, said metathesized unsaturated polyol ester has the iodine value property from a)(iii) above. |
| 5 | In one aspect of said composition 1 of Table 2, said metathesized unsaturated polyol ester has the property from a)(i) and from a)(ii) above. |
| 6 | In one aspect of said composition 1 of Table 2, said metathesized unsaturated polyol ester has the properties from a)(i) and from a)(iii) above. |
| 7 | In one aspect of said composition 1 of Table 2, said metathesized unsaturated polyol ester has the properties from a)(ii) and from a)(iii) above. |
| 8 | In one aspect of said composition 1 of Table 2, said metathesized unsaturated polyol ester has the properties from a)(i), a)(ii) and from a)(iii) above. |

TABLE 2-continued

Liquid Compositions

| Comp. No. | Composition |
|---|---|
| 9 | In one aspect of Table 2 Compositions 1, 2, 3, 4, 5, 6, 7, and 8 the metathesized unsaturated polyol ester is metathesized at least once. |
| 10 | In one aspect, of compositions 1, 2, 3, 4, 5, 6, 7, and 9 of Table 2, said composition comprises, based on total composition weight, from about 0.01% to about 10%, from about 0.1% to about 8%, or from about 0.2% to about 4% of said metathesized unsaturated polyol ester. |

In one aspect, Table 1 Compositions 1, 2, 3, 4, 5, 6, 7, 8, 9, 10 and 11; and Table 2 Compositions 1, 2, 3, 4, 5, 6, 7, 8, 9 and 10 comprise one or more of the following:
a) from about 0.01% to about 10%, from about 0.1% to about 8%, or from about 0.2% to about 4% of an emollient;
b) from about 0.1% to about 5%, by weight of the liquid composition, of clay mineral;
c) from about 0.01% to about 5%, from about 0.02% to about 0.5%, or from about 0.05% to about 0.2% by weight of the liquid composition, of a rheology modifier;
d) from about 0.0% to about 10%, or about 0.1% to about 5%, or about 0.3% to about 3% by weight of an emulsifier;
e) from about 0.1% to about 4%, or about 0.3% to about 2%, or about 0.5% to about 1% by weight of a preservative.
f) a perfume.
g) from about 0.1% to about 2.0% of a pH adjusting agents and pH buffering system, or from about 0.3% to about 1.5%, or from about 0.5% to about 1.5%.

In one aspect, Table 1 Compositions 1, 2, 3, 4, 5, 6, 7, 8, 9, 10 and 11; and Table 2 Compositions 1, 2, 3, 4, 5, 6, 7, 8, 9 and 10 the metathesized unsaturated polyol ester is derived from a natural polyol ester and/or a synthetic polyol ester, in one aspect, said natural polyol ester is selected from the group consisting of a vegetable oil, an animal fat, an algae oil and mixtures thereof; and said synthetic polyol ester is derived from a material selected from the group consisting of ethylene glycol, propylene glycol, glycerol, polyglycerol, polyethylene glycol, polypropylene glycol, poly(tetramethylene ether) glycol, pentaerythritol, dipentaerythritol, tripentaerythritol, trimethylolpropane, neopentyl glycol, a sugar, in one aspect, sucrose, and mixtures thereof.

In one aspect, Table 1 Compositions 1, 2, 3, 4, 5, 6, 7, 8, 9, 10 and 11; and Table 2 Compositions 1, 2, 3, 4, 5, 6, 7, 8, 9 and 10 the metathesized unsaturated polyol ester is selected from the group consisting of metathesized Abyssinian oil, metathesized Almond Oil, metathesized Apricot Oil, metathesized Apricot Kernel oil, metathesized Argan oil, metathesized Avocado Oil, metathesized Babassu Oil, metathesized Baobab Oil, metathesized Black Cumin Oil, metathesized Black Currant Oil, metathesized Borage Oil, metathesized Camelina oil, metathesized Carinata oil, metathesized Canola oil, metathesized Castor oil, metathesized Cherry Kernel Oil, metathesized Coconut oil, metathesized Corn oil, metathesized Cottonseed oil, metathesized Echium Oil, metathesized Evening Primrose Oil, metathesized Flax Seed Oil, metathesized Grape Seed Oil, metathesized Grapefruit Seed Oil, metathesized Hazelnut Oil, metathesized Hemp Seed Oil, metathesized Jatropha oil, metathesized Jojoba Oil, metathesized Kukui Nut Oil, metathesized Linseed Oil, metathesized Macadamia Nut Oil, metathesized Meadowfoam Seed Oil, metathesized Moringa Oil, metathesized Neem Oil, metathesized Olive Oil, metathesized Palm Oil, metathesized Palm Kernel Oil, metathesized Peach Kernel Oil, metathesized Peanut Oil, metathesized Pecan Oil, metathesized Pennycress oil, metathesized Perilla Seed Oil, metathesized Pistachio Oil, metathesized Pomegranate Seed Oil, metathesized Pongamia oil, metathesized Pumpkin Seed Oil, metathesized Raspberry Oil, metathesized Red Palm Olein, metathesized Rice Bran Oil, metathesized Rosehip Oil, metathesized Safflower Oil, metathesized Seabuckthorn Fruit Oil, metathesized Sesame Seed Oil, metathesized Shea Olein, metathesized Sunflower Oil, metathesized Soybean Oil, metathesized Tonka Bean Oil, metathesized Tung Oil, metathesized Walnut Oil, metathesized Wheat Germ Oil, metathesized High Oleoyl Soybean Oil, metathesized High Oleoyl Sunflower Oil, metathesized High Oleoyl Safflower Oil, metathesized High Erucic Acid Rapeseed Oil, and mixtures thereof.

In one aspect, the compositions disclosed herein, including Table 1 Compositions 1, 2, 3, 4, 5, 6, 7, 8, 9, 10 and 11; and Table 2 Compositions 1, 2, 3, 4, 5, 6, 7, 8, 9 and 10 comprise:
a) an emulsifier and an emollient; or
b) an emulsifier, an emollient and a preservative; or
c) an emulsifier, an emollient, a rheology modifier, a perfume and a preservative; or
d) an emollient and a clay mineral; or
e) an emulsifier, an emollient, a rheology modifier and a preservative.

The liquid compositions may comprise greater than about 80%, greater than about 85%, greater than about 90%, or greater than about 95% water, by weight of the liquid composition. The pH of the composition may be from about pH 3, 4, or 5 to about pH 7, 7.5, or 8. In some exemplary configurations, the pH may be from about 3.5 to about 4.5.

In addition, the liquid composition may include various optional ingredients, such as film-formers, skin treatment actives, pH buffers, anti-oxidants, metal sequestrants, particulates, perfumes and various other adjunct ingredients, such as described in U.S. Pat. Nos. 7,666,827; 7,005,557; 8,221,774; and U.S. Patent Application Publication No. 2011/0268777. It is to be noted that some ingredient compounds can have a multiple function and that all compounds are not necessarily present in the liquid composition.

Methods of Making Compositions

The compositions of the present invention can be formulated into any suitable form and prepared by any process chosen by the formulator. For example, the metathesized unsaturated polyol esters can be combined directly with the composition's other ingredients without pre-emulsification and/or pre-mixing to form the finished products. Alternatively, the metathesized unsaturated polyol esters can be combined with surfactants or emulsifiers, solvents, suitable adjuncts, and/or any other suitable ingredients to prepare emulsions prior to compounding the finished products.

Wipes are generally impregnated with a liquid or semi liquid composition, intended to both enhance the cleaning and to provide a smooth feeling. Generally the composition is of sufficiently low viscosity to impregnate the entire structure of the wipe. In some other instances, the composition can be primarily present at the wipe surface and to a lesser extent in the inner structure of the wipe. In one optional embodiment the composition is releasably carried by the material, that is, the composition is contained either in or on a substrate and is readily releasable from the substrate by applying some force to the substrate, for example, wringing the substrate, or wiping a surface, such as a child's bottom, with the wet-wipe.

The compositions of the present invention, and wipes comprising the compositions, can be made by the conventional processes described in the art. Alternatively, the composition and wipes are made according to U.S. Provisional Patent Application No. 60/520,032 entitled "A process for making a wet wipe using a concentrated emulsion" by Sylvie Chamba et al., Procter & Gamble.

Metathesized Unsaturated Polyol Ester

Exemplary metathesized unsaturated polyol esters and their starting materials are set forth in U.S. Patent Applications U.S. 2009/0220443 A1, U.S. 2013/0344012 A1 and US 2014/0357714 A1, which are incorporated herein by reference. A metathesized unsaturated polyol ester refers to the product obtained when one or more unsaturated polyol ester ingredient(s) are subjected to a metathesis reaction. Metathesis is a catalytic reaction that involves the interchange of alkylidene units among compounds containing one or more double bonds (i.e., olefinic compounds) via the formation and cleavage of the carbon-carbon double bonds. Metathesis may occur between two of the same molecules (often referred to as self-metathesis) and/or it may occur between two different molecules (often referred to as cross-metathesis). Self-metathesis may be represented schematically as shown in Equation I.

where $R^1$ and $R^2$ are organic groups.

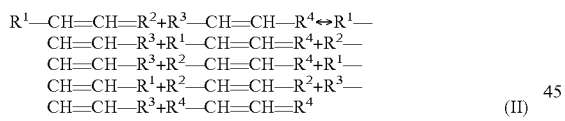

Cross-metathesis may be represented schematically as shown in Equation II.

where $R^1$, $R^2$, $R^3$, and $R^4$ are organic groups.

When a polyol ester comprises molecules having more than one carbon-carbon double bond, self-metathesis may result in oligomerization or polymerization of the unsaturates in the starting material. For example, Equation C depicts metathesis oligomerization of a representative species (e.g., a polyol ester) having more than one carbon-carbon double bond. In Equation C, the self-metathesis reaction results in the formation of metathesis dimers, metathesis trimers, and metathesis tetramers. Although not shown, higher order oligomers such as metathesis pentamers, hexamers, heptamers, octamers, nonamers, decamers, and higher than decamers, and mixtures of two or more thereof, may also be formed. The number of metathesis repeating units or groups in the metathesized natural oil may range from 1 to about 100, or from 2 to about 50, or from 2 to about 30, or from 2 to about 10, or from 2 to about 4. The molecular weight of the metathesis dimer may be greater than the molecular weight of the unsaturated polyol ester from which the dimer is formed. Each of the bonded polyol ester molecules may be referred to as a "repeating unit or group." Typically, a metathesis trimer may be formed by the cross-metathesis of a metathesis dimer with an unsaturated polyol ester. Typically, a metathesis tetramer may be formed by the cross-metathesis of a metathesis trimer with an unsaturated polyol ester or formed by the cross-metathesis of two metathesis dimers.

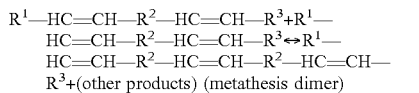

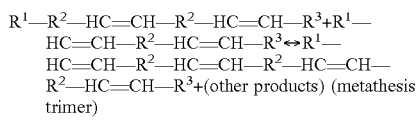

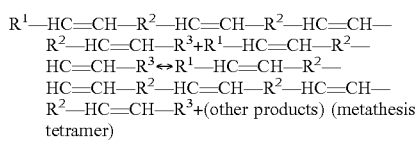

Equation C where $R^1$, $R^2$, and $R^3$ are organic groups.

As a starting material, metathesized unsaturated polyol esters are prepared from one or more unsaturated polyol esters. As used herein, the term "unsaturated polyol ester" refers to a compound having two or more hydroxyl groups wherein at least one of the hydroxyl groups is in the form of an ester and wherein the ester has an organic group including at least one carbon-carbon double bond. In many embodiments, the unsaturated polyol ester can be represented by the general structure (I):

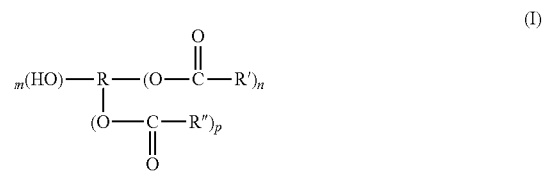

where n≥1;
m≥0;
p≥0;
(n+m+p)≤2;
R is an organic group;
R' is an organic group having at least one carbon-carbon double bond; and
R" is a saturated organic group.

In many embodiments of the invention, the unsaturated polyol ester is an unsaturated polyol ester of glycerol. Unsaturated polyol esters of glycerol have the general structure (II):

where —X, —Y, and —Z are independently selected from the group consisting of:
—OH; —(O—C(=O)—R'); and —(O—C(=O)—R");
where —R' is an organic group having at least one carbon-carbon double bond and —R" is a saturated organic group.

In structure (II), at least one of —X, —Y, and —Z is —O—C(=O)—R').

In some embodiments, R' is a straight or branched chain hydrocarbon having about 50 or less carbon atoms (e.g., about 36 or less carbon atoms or about 26 or less carbon atoms) and at least one carbon-carbon double bond in its chain. In some embodiments, R' is a straight or branched chain hydrocarbon having about 6 carbon atoms or greater (e.g., about 10 carbon atoms or greater or about 12 carbon atoms or greater) and at least one carbon-carbon double bond in its chain. In some embodiments, R' may have two or more carbon-carbon double bonds in its chain. In other embodiments, R' may have three or more double bonds in its chain. In exemplary embodiments, R' has 17 carbon atoms and 1 to 3 carbon-carbon double bonds in its chain. Representative examples of R' include:

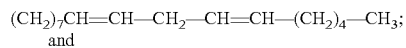
and

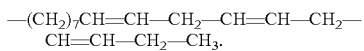

In some embodiments, R" is a saturated straight or branched chain hydrocarbon having about 50 or less carbon atoms (e.g., about 36 or less carbon atoms or about 26 or less carbon atoms). In some embodiments, R" is a saturated straight or branched chain hydrocarbon having about 6 carbon atoms or greater (e.g., about 10 carbon atoms or greater or about 12 carbon atoms or greater. In exemplary embodiments, R" has 15 carbon atoms or 17 carbon atoms.

Sources of unsaturated polyol esters of glycerol include synthesized oils, natural oils (e.g., vegetable oils, algae oils, bacterial derived oils, and animal fats), combinations of these, and the like. Recycled used vegetable oils may also be used. Representative non-limiting examples of vegetable oils include Abyssinian oil, Almond Oil, Apricot Oil, Apricot Kernel oil, Argan oil, Avocado Oil, Babassu Oil, Baobab Oil, Black Cumin Oil, Black Currant Oil, Borage Oil, Camelina oil, Carinata oil, Canola oil, Castor oil, Cherry Kernel Oil, Coconut oil, Corn oil, Cottonseed oil, Echium Oil, Evening Primrose Oil, Flax Seed Oil, Grape Seed Oil, Grapefruit Seed Oil, Hazelnut Oil, Hemp Seed Oil, Jatropha oil, Jojoba Oil, Kukui Nut Oil, Linseed Oil, Macadamia Nut Oil, Meadowfoam Seed Oil, Moringa Oil, Neem Oil, Olive Oil, Palm Oil, Palm Kernel Oil, Peach Kernel Oil, Peanut Oil, Pecan Oil, Pennycress oil, Perilla Seed Oil, Pistachio Oil, Pomegranate Seed Oil, Pongamia oil, Pumpkin Seed Oil, Raspberry Oil, Red Palm Olein, Rice Bran Oil, Rosehip Oil, Safflower Oil, Seabuckthorn Fruit Oil, Sesame Seed Oil, Shea Olein, Sunflower Oil, Soybean Oil, Tonka Bean Oil, Tung Oil, Walnut Oil, Wheat Germ Oil, High Oleoyl Soybean Oil, High Oleoyl Sunflower Oil, High Oleoyl Safflower Oil, High Erucic Acid Rapeseed Oil, combinations of these, and the like. Representative non-limiting examples of animal fats include lard, tallow, chicken fat, yellow grease, fish oil, emu oil, combinations of these, and the like. A representative non-limiting example of a synthesized oil includes tall oil, which is a byproduct of wood pulp manufacture. In some embodiments, the natural oil is refined, bleached, and/or deodorized.

Other examples of unsaturated polyol esters include esters such as those derived from ethylene glycol or propylene glycol, polyethylene glycol, polypropylene glycol, or poly (tetramethylene ether) glycol, esters such as those derived from pentaerythritol, dipentaerythritol, tripentaerythritol, trimethylolpropane, or neopentyl glycol, or sugar esters such as SEFOSE®. Sugar esters such as SEFOSE® include one or more types of sucrose polyesters, with up to eight ester groups that could undergo a metathesis exchange reaction. Sucrose polyesters are derived from a natural resource and therefore, the use of sucrose polyesters can result in a positive environmental impact. Sucrose polyesters are polyester materials, having multiple substitution positions around the sucrose backbone coupled with the chain length, saturation, and derivation variables of the fatty chains. Such sucrose polyesters can have an esterification ("IBAR") of greater than about 5. In one embodiment the sucrose polyester may have an IBAR of from about 5 to about 8. In another embodiment the sucrose polyester has an IBAR of about 5-7, and in another embodiment the sucrose polyester has an IBAR of about 6. In yet another embodiment the sucrose polyester has an IBAR of about 8. As sucrose polyesters are derived from a natural resource, a distribution in the IBAR and chain length may exist. For example a sucrose polyester having an IBAR of 6, may contain a mixture of mostly IBAR of about 6, with some IBAR of about 5 and some IBAR of about 7. Additionally, such sucrose polyesters may have a saturation or iodine value ("IV") of about 3 to about 140. In another embodiment the sucrose polyester may have an IV of about 10 to about 120. In yet another embodiment the sucrose polyester may have an IV of about 20 to 100. Further, such sucrose polyesters have a chain length of about $C_{12}$ to $C_{20}$ but are not limited to these chain lengths.

Non-limiting examples of sucrose polyesters suitable for use include SEFOSE® 1618S, SEFOSE® 1618U, SEFOSE® 1618H, Sefa Soyate IMF 40, Sefa Soyate LP426, SEFOSE® 2275, SEFOSE® C1695, SEFOSE® C18:0 95, SEFOSE® C1495, SEFOSE® 1618H B6, SEFOSE® 1618S B6, SEFOSE® 1618U B6, Sefa Cottonate, SEFOSE® C1295, Sefa C895, Sefa C1095, SEFOSE® 1618S B4.5, all available from The Procter and Gamble Co. of Cincinnati, Ohio.

Other examples of suitable polyol esters may include but not be limited to sorbitol esters, maltitol esters, sorbitan esters, maltodextrin derived esters, xylitol esters, polyglycerol esters, and other sugar derived esters.

Natural oils of the type described herein typically are composed of triglycerides of fatty acids. These fatty acids may be either saturated, monounsaturated or polyunsaturated and contain varying chain lengths ranging from $C_8$ to $C_{30}$. The most common fatty acids include saturated fatty acids such as lauric acid (dodecanoic acid), myristic acid (tetradecanoic acid), palmitic acid (hexadecanoic acid), stearic acid (octadecanoic acid), arachidic acid (eicosanoic acid), and lignoceric acid (tetracosanoic acid); unsaturated acids include such fatty acids as palmitoleic (a $C_{16}$ acid), and oleic acid (a $C_{18}$ acid); polyunsaturated acids include such fatty acids as linoleic acid (a di-unsaturated $C_{18}$ acid), linolenic acid (a tri-unsaturated $C_{18}$ acid), and arachidonic acid (a tetra-unsubstituted $C_{20}$ acid). The natural oils are further comprised of esters of these fatty acids in random placement onto the three sites of the trifunctional glycerine molecule. Different natural oils will have different ratios of these fatty acids, and within a given natural oil there is a range of these acids as well depending on such factors as where a vegetable or crop is grown, maturity of the vegetable or crop, the weather during the growing season, etc. Thus, it is difficult to have a specific or unique structure for any given natural oil, but rather a structure is typically based on some statistical average. For example soybean oil contains a mixture of stearic acid, oleic acid, linoleic acid, and linolenic acid in the ratio of 15:24:50:11, and an average number of double bonds of 4.4-4.7 per triglyceride. One method of quantifying the number of double bonds is the iodine value (IV) which is defined as the number of grams of iodine that will react with 100 grams of oil. Therefore for soybean oil, the average iodine value range is from 120-140. Soybean oil may comprises about 95% by weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9,12octadecadienoic acid), and linolenic acid (9,12,15-octadecatrienoic acid).

In an exemplary embodiment, the vegetable oil is canola oil, for example, refined, bleached, and deodorized canola oil (i.e., RBD canola oil). Canola oil is an unsaturated polyol ester of glycerol that typically comprises about 95% weight or greater (e.g., 99% weight or greater) triglycerides of fatty acids. Major fatty acids in the polyol esters of canola oil include saturated fatty acids, for example, palmitic acid (hexadecanoic acid) and stearic acid (octadecanoic acid), and unsaturated fatty acids, for example, oleic acid (9-octadecenoic acid), linoleic acid (9,12-octadecadienoic acid), and linolenic acid (9,12,15-octadecatrienoic acid). Canola oil is a highly unsaturated vegetable oil with many of the triglyceride molecules having at least two unsaturated fatty acids (i.e., a polyunsaturated triglyceride).

In exemplary embodiments, an unsaturated polyol ester is self-metathesized in the presence of a metathesis catalyst to form a metathesized composition. Typically, after metathesis has occurred, the metathesis catalyst is removed from the resulting product. One method of removing the catalyst is treatment of the metathesized product with clay. In many embodiments, the metathesized composition comprises one or more of: metathesis monomers, metathesis dimers, metathesis trimers, metathesis tetramers, metathesis pentamers, and higher order metathesis oligomers (e.g., metathesis hexamers). A metathesis dimer refers to a compound formed when two unsaturated polyol ester molecules are covalently bonded to one another by a self-metathesis reaction. In many embodiments, the molecular weight of the metathesis dimer is greater than the molecular weight of the individual unsaturated polyol ester molecules from which the dimer is formed. A metathesis trimer refers to a compound formed when three unsaturated polyol ester molecules are covalently bonded together by metathesis reactions. In many embodiments, a metathesis trimer is formed by the cross-metathesis of a metathesis dimer with an unsaturated polyol ester. A metathesis tetramer refers to a compound formed when four unsaturated polyol ester molecules are covalently bonded together by metathesis reactions. In many embodiments, a metathesis tetramer is formed by the cross-metathesis of a metathesis trimer with an unsaturated polyol ester. Metathesis tetramers may also be formed, for example, by the cross-metathesis of two metathesis dimers. Higher order metathesis products may also be formed. For example, metathesis pentamers and metathesis hexamers may also be formed. The self-metathesis reaction also results in the formation of internal olefin compounds that may be linear or cyclic. If the metathesized polyol ester is fully or partially hydrogenated, the linear and cyclic olefins would typically be fully or partially converted to the corresponding saturated linear and cyclic hydrocarbons. The linear/cyclic olefins and saturated linear/cyclic hydrocarbons may remain in the metathesized polyol ester or they may be removed or partially removed from the metathesized polyol ester using one or more known stripping techniques, including but not limited to wipe film evaporation, falling film evaporation, rotary evaporation, steam stripping, vacuum distillation, etc.

In some embodiments, the unsaturated polyol ester is partially hydrogenated before being metathesized. For example, in some embodiments, the unsaturated polyol ester is partially hydrogenated to achieve an iodine value (IV) of about 120 or less before subjecting the partially hydrogenated polyol ester to metathesis.

In some embodiments, the unsaturated polyol ester may be hydrogenated (e.g., fully or partially hydrogenated) in order to improve the stability of the oil or to modify its viscosity or other properties. Representative techniques for hydrogenating unsaturated polyol esters are known in the art and are discussed herein.

In some embodiments, the natural oil is winterized. Winterization refers to the process of: (1) removing waxes and other non-triglyceride constituents, (2) removing naturally occurring high-melting triglycerides, and (3) removing high-melting triglycerides formed during partial hydrogenation. Winterization may be accomplished by known methods including, for example, cooling the oil at a controlled rate in order to cause crystallization of the higher melting components that are to be removed from the oil. The crystallized high melting components are then removed from the oil by filtration resulting in winterized oil. Winterized soybean oil is commercially available from Cargill, Incorporated (Minneapolis, Minn.).

In other embodiments, the metathesized unsaturated polyol esters can be used as a blend with one or more fabric care benefit agents and/or fabric softening actives.

Method of Making Metathesized Unsaturated Polyol Ester

The self-metathesis of unsaturated polyol esters is typically conducted in the presence of a catalytically effective amount of a metathesis catalyst. The term "metathesis catalyst" includes any catalyst or catalyst system that catalyzes a metathesis reaction. Any known or future-developed metathesis catalyst may be used, alone or in combination with one or more additional catalysts. Suitable homogeneous metathesis catalysts include combinations of a transition metal halide or oxo-halide (e.g., $WOCl_4$ or $WCl_6$) with an alkylating cocatalyst (e.g., $Me_4Sn$), or alkylidene (or carbene) complexes of transition metals, particularly Ru or W. These include first and second-generation Grubbs catalysts, Grubbs-Hoveyda catalysts, and the like. Suitable alkylidene catalysts have the general structure: $M[X^1X^2L^1L^2(L^3)_n]=C_m=C(R^1)R^2$ where M is a Group 8 transition metal, $L^1$, $L^2$, and $L^3$ are neutral electron donor ligands, n is 0 (such that $L^3$ may not be present) or 1, m is 0, 1, or 2, $X^1$ and $X^2$ are anionic ligands, and $R^1$ and $R^2$ are independently selected from H, hydrocarbyl, substituted hydrocarbyl, heteroatom-containing hydrocarbyl, substituted heteroatom-containing hydrocarbyl, and functional groups. Any two or more of $X^1$, $X^2$, $L_1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^1$, $L^2$, $L^3$, $R^1$ and $R^2$ as described in U.S. Pat. Appl. Publ. No. 2010/0145086, the teachings of which related to all metathesis catalysts are incorporated herein by reference.

Second-generation Grubbs catalysts also have the general formula described above, but $L^1$ is a carbene ligand where the carbene carbon is flanked by N, O, S, or P atoms, preferably by two N atoms. Usually, the carbene ligand is part of a cyclic group. Examples of suitable second-generation Grubbs catalysts also appear in the '086 publication.

In another class of suitable alkylidene catalysts, $L^1$ is a strongly coordinating neutral electron donor as in first- and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like.

In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^2$ are linked. Typically, a neutral oxygen or nitrogen coordinates to the metal while also being bonded to a carbon that is α-, β-, or γ- with respect to the carbene carbon to provide the bidentate ligand. Examples of suitable Grubbs-Hoveyda catalysts appear in the '086 publication.

The structures below provide just a few illustrations of suitable catalysts that may be used:

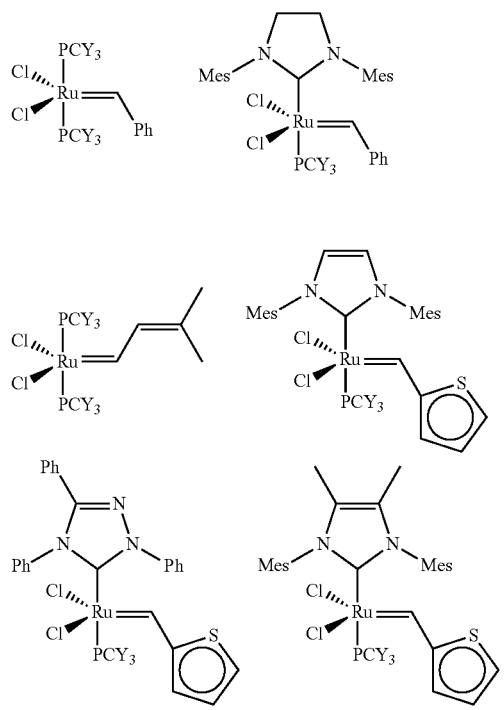

An immobilized catalyst can be used for the metathesis process. An immobilized catalyst is a system comprising a catalyst and a support, the catalyst associated with the support. Exemplary associations between the catalyst and the support may occur by way of chemical bonds or weak interactions (e.g. hydrogen bonds, donor acceptor interactions) between the catalyst, or any portions thereof, and the support or any portions thereof. Support is intended to include any material suitable to support the catalyst. Typically, immobilized catalysts are solid phase catalysts that act on liquid or gas phase reactants and products. Exemplary supports are polymers, silica or alumina. Such an immobilized catalyst may be used in a flow process. An immobilized catalyst can simplify purification of products and recovery of the catalyst so that recycling the catalyst may be more convenient.

In certain embodiments, prior to the metathesis reaction, the unsaturated polyol ester feedstock may be treated to render the natural oil more suitable for the subsequent metathesis reaction. In one embodiment, the treatment of the unsaturated polyol ester involves the removal of catalyst poisons, such as peroxides, which may potentially diminish the activity of the metathesis catalyst. Non-limiting examples of unsaturated polyol ester feedstock treatment methods to diminish catalyst poisons include those described in PCT/US2008/09604, PCT/US2008/09635, and U.S. patent application Ser. Nos. 12/672,651 and 12/672,652, herein incorporated by reference in their entireties. In certain embodiments, the unsaturated polyol ester feedstock is thermally treated by heating the feedstock to a temperature greater than 100° C. in the absence of oxygen and held at the temperature for a time sufficient to diminish catalyst poisons in the feedstock. In other embodiments, the temperature is between approximately 100° C. and 300° C., between approximately 120° C. and 250° C., between approximately 150° C. and 210° C., or approximately between 190 and 200° C. In one embodiment, the absence of oxygen is achieved by sparging the unsaturated polyol ester feedstock with nitrogen, wherein the nitrogen gas is pumped into the feedstock treatment vessel at a pressure of approximately 10 atm (150 psig).

In certain embodiments, the unsaturated polyol ester feedstock is chemically treated under conditions sufficient to diminish the catalyst poisons in the feedstock through a chemical reaction of the catalyst poisons. In certain embodiments, the feedstock is treated with a reducing agent or a cation-inorganic base composition. Non-limiting examples of reducing agents include bisulfate, borohydride, phosphine, thiosulfate, and combinations thereof.

In certain embodiments, the unsaturated polyol ester feedstock is treated with an adsorbent to remove catalyst poisons. In one embodiment, the feedstock is treated with a combination of thermal and adsorbent methods. In another embodiment, the feedstock is treated with a combination of chemical and adsorbent methods. In another embodiment, the treatment involves a partial hydrogenation treatment to modify the unsaturated polyol ester feedstock's reactivity with the metathesis catalyst. Additional non-limiting examples of feedstock treatment are also described below when discussing the various metathesis catalysts.

In certain embodiments, a ligand may be added to the metathesis reaction mixture. In many embodiments using a ligand, the ligand is selected to be a molecule that stabilizes the catalyst, and may thus provide an increased turnover number for the catalyst. In some cases the ligand can alter reaction selectivity and product distribution. Examples of ligands that can be used include Lewis base ligands, such as, without limitation, trialkylphosphines, for example tricyclohexylphosphine and tributyl phosphine; triarylphosphines, such as triphenylphosphine; diarylalkylphosphines, such as, diphenylcyclohexylphosphine; pyridines, such as 2,6-dimethylpyridine, 2,4,6-trimethylpyridine; as well as other Lewis basic ligands, such as phosphine oxides and phosphinites. Additives may also be present during metathesis that increase catalyst lifetime.

Any useful amount of the selected metathesis catalyst can be used in the process. For example, the molar ratio of the unsaturated polyol ester to catalyst may range from about 5:1 to about 10,000,000:1 or from about 50:1 to 500,000:1. In some embodiments, an amount of about 1 to about 10 ppm, or about 2 ppm to about 5 ppm, of the metathesis catalyst per double bond of the starting composition (i.e., on a mole/mole basis) is used.

In some embodiments, the metathesis reaction is catalyzed by a system containing both a transition and a non-transition metal component. The most active and largest number of catalyst systems are derived from Group VI A transition metals, for example, tungsten and molybdenum.

Multiple, sequential metathesis reaction steps may be employed. For example, the metathesized unsaturated polyol ester product may be made by reacting an unsaturated polyol ester in the presence of a metathesis catalyst to form a first metathesized unsaturated polyol ester product. The first metathesized unsaturated polyol ester product may then be reacted in a self-metathesis reaction to form another metathesized unsaturated polyol ester product. Alternatively, the first metathesized unsaturated polyol ester product may be reacted in a cross-metathesis reaction with a unsaturated polyol ester to form another metathesized unsaturated polyol ester product. Also in the alternative, the transesterified products, the olefins and/or esters may be further metathesized in the presence of a metathesis catalyst. Such multiple and/or sequential metathesis reactions can be performed as many times as needed, and at least one or more times, depending on the processing/compositional requirements as understood by a person skilled in the art. As used herein, a "metathesized unsaturated polyol ester product" may include products that have been once metathesized and/or multiply metathesized. These procedures may be used to form metathesis dimers, metathesis trimers, metathesis tetramers, metathesis pentamers, and higher order metathesis oligomers (e.g., metathesis hexamers, metathesis heptamers, metathesis octamers, metathesis nonamers, metathesis decamers, and higher than metathesis decamers). These procedures can be repeated as many times as desired (for example, from 2 to about 50 times, or from 2 to about 30 times, or from 2 to about 10 times, or from 2 to about 5 times, or from 2 to about 4 times, or 2 or 3 times) to provide the desired metathesis oligomer or polymer which may comprise, for example, from 2 to about 100 bonded groups, or from 2 to about 50, or from 2 to about 30, or from 2 to about 10, or from 2 to about 8, or from 2 to about 6 bonded groups, or from 2 to about 4 bonded groups, or from 2 to about 3 bonded groups. In certain embodiments, it may be desirable to use the metathesized unsaturated polyol ester products produced by cross metathesis of an unsaturated polyol ester, or blend of unsaturated polyol esters, with a C2-C100 olefin, as the reactant in a self-metathesis reaction to produce another metathesized unsaturated polyol ester product. Alternatively, metathesized products produced by cross metathesis of an unsaturated polyol ester, or blend of unsaturated polyol esters, with a C2-C100 olefin can be combined with an unsaturated polyol ester, or blend of unsaturated polyol esters, and further metathesized to produce another metathesized unsaturated polyol ester product.

The metathesis process can be conducted under any conditions adequate to produce the desired metathesis products. For example, stoichiometry, atmosphere, solvent, temperature, and pressure can be selected by one skilled in the art to produce a desired product and to minimize undesirable byproducts. The metathesis process may be conducted under an inert atmosphere. Similarly, if a reagent is supplied as a gas, an inert gaseous diluent can be used. The inert atmosphere or inert gaseous diluent typically is an inert gas, meaning that the gas does not interact with the metathesis catalyst to substantially impede catalysis. For example, particular inert gases are selected from the group consisting of helium, neon, argon, nitrogen, individually or in combinations thereof.

In certain embodiments, the metathesis catalyst is dissolved in a solvent prior to conducting the metathesis reaction. In certain embodiments, the solvent chosen may be selected to be substantially inert with respect to the metathesis catalyst. For example, substantially inert solvents include, without limitation, aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc. In one particular embodiment, the solvent comprises toluene. The metathesis reaction temperature may be a rate-controlling variable where the temperature is selected to provide a desired product at an acceptable rate. In certain embodiments, the metathesis reaction temperature is greater than about −40° C., greater than about −20° C., greater than about 0° C., or greater than about 10° C. In certain embodiments, the metathesis reaction temperature is less than about 150° C., or less than about 120° C. In one embodiment, the metathesis reaction temperature is between about 10° C. and about 120° C.

The metathesis reaction can be run under any desired pressure. Typically, it will be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than about 0.1 atm (10 kPa), in some embodiments greater than about 0.3 atm (30 kPa), or greater than about 1 atm (100 kPa). Typically, the reaction pressure is no more than about 70 atm (7000 kPa), in some embodiments no more than about 30 atm (3000 kPa). A non-limiting exemplary pressure range for the metathesis reaction is from about 1 atm (100 kPa) to about 30 atm (3000 kPa). In certain embodiments it may be desirable to run the metathesis reactions under an atmosphere of reduced pressure. Conditions of reduced pressure or vacuum may be used to remove olefins as they are generated in a metathesis reaction, thereby driving the metathesis equilibrium towards the formation of less volatile products. In the case of a self-metathesis of a natural oil, reduced pressure can be used to remove $C_{12}$ or lighter olefins including, but not limited to, hexene, nonene, and dodecene, as well as byproducts including, but not limited to cyclohexa-diene and benzene as the metathesis reaction proceeds. The removal of these species can be used as a means to drive the reaction towards the formation of diester groups and cross linked triglycerides.

Hydrogenation:

In some embodiments, the unsaturated polyol ester is partially hydrogenated before it is subjected to the metathesis reaction. Partial hydrogenation of the unsaturated polyol ester reduces the number of double bonds that are available for in the subsequent metathesis reaction. In some embodiments, the unsaturated polyol ester is metathesized to form a metathesized unsaturated polyol ester, and the metathesized unsaturated polyol ester is then hydrogenated (e.g., partially or fully hydrogenated) to form a hydrogenated metathesized unsaturated polyol ester.

Hydrogenation may be conducted according to any known method for hydrogenating double bond-containing compounds such as vegetable oils. In some embodiments, the unsaturated polyol ester or metathesized unsaturated polyol ester is hydrogenated in the presence of a nickel catalyst that has been chemically reduced with hydrogen to an active state. Commercial examples of supported nickel hydrogenation catalysts include those available under the trade designations "NYSOFACT", "NYSOSEL", and "NI 5248 D" (from Englehard Corporation, Iselin, N.H.). Additional supported nickel hydrogenation catalysts include those commercially available under the trade designations "PRICAT 9910", "PRICAT 9920", "PRICAT 9908", "PRICAT 9936" (from Johnson Matthey Catalysts, Ward Hill, Mass.).

In some embodiments, the hydrogenation catalyst comprising, for example, nickel, copper, palladium, platinum, molybdenum, iron, ruthenium, osmium, rhodium, or iridium. Combinations of metals may also be used. Useful catalyst may be heterogeneous or homogeneous. In some embodiments, the catalysts are supported nickel or sponge nickel type catalysts.

In some embodiments, the hydrogenation catalyst comprises nickel that has been chemically reduced with hydrogen to an active state (i.e., reduced nickel) provided on a support. In some embodiments, the support comprises porous silica (e.g., kieselguhr, infusorial, diatomaceous, or siliceous earth) or alumina. The catalysts are characterized by a high nickel surface area per gram of nickel.

In some embodiments, the particles of supported nickel catalyst are dispersed in a protective medium comprising hardened triacylglyceride, edible oil, or tallow. In an exemplary embodiment, the supported nickel catalyst is dispersed in the protective medium at a level of about 22 wt. % nickel.

Hydrogenation may be carried out in a batch or in a continuous process and may be partial hydrogenation or complete hydrogenation. In a representative batch process, a vacuum is pulled on the headspace of a stirred reaction vessel and the reaction vessel is charged with the material to be hydrogenated (e.g., RBD soybean oil or metathesized RBD soybean oil). The material is then heated to a desired temperature. Typically, the temperature ranges from about 50 deg. C. to 350 deg. C., for example, about 100 deg. C. to 300 deg. C. or about 150 deg. C. to 250 deg. C. The desired temperature may vary, for example, with hydrogen gas pressure. Typically, a higher gas pressure will require a lower temperature. In a separate container, the hydrogenation catalyst is weighed into a mixing vessel and is slurried in a small amount of the material to be hydrogenated (e.g., RBD soybean oil or metathesized RBD soybean oil). When the material to be hydrogenated reaches the desired temperature, the slurry of hydrogenation catalyst is added to the reaction vessel. Hydrogen gas is then pumped into the reaction vessel to achieve a desired pressure of H2 gas. Typically, the H2 gas pressure ranges from about 15 to 3000 psig, for example, about 15 psig to 90 psig. As the gas pressure increases, more specialized high-pressure processing equipment may be required. Under these conditions the hydrogenation reaction begins and the temperature is allowed to increase to the desired hydrogenation temperature (e.g., about 120 deg. C. to 200 deg. C.) where it is maintained by cooling the reaction mass, for example, with cooling coils. When the desired degree of hydrogenation is reached, the reaction mass is cooled to the desired filtration temperature.

The amount of hydrogenation catalysts is typically selected in view of a number of factors including, for example, the type of hydrogenation catalyst used, the amount of hydrogenation catalyst used, the degree of unsaturation in the material to be hydrogenated, the desired rate of hydrogenation, the desired degree of hydrogenation (e.g., as measure by iodine value (IV)), the purity of the reagent, and the H2 gas pressure. In some embodiments, the hydrogenation catalyst is used in an amount of about 10 wt. % or less, for example, about 5 wt. % or less or about 1 wt. % or less.

After hydrogenation, the hydrogenation catalyst may be removed from the hydrogenated product using known techniques, for example, by filtration. In some embodiments, the hydrogenation catalyst is removed using a plate and frame filter such as those commercially available from Sparkler Filters, Inc., Conroe Tex. In some embodiments, the filtration is performed with the assistance of pressure or a vacuum. In order to improve filtering performance, a filter aid may be used. A filter aid may be added to the metathesized product directly or it may be applied to the filter. Representative examples of filtering aids include diatomaceous earth, silica, alumina, and carbon. Typically, the filtering aid is used in an amount of about 10 wt. % or less, for example, about 5 wt. % or less or about 1 wt. % or less. Other filtering techniques and filtering aids may also be employed to remove the used hydrogenation catalyst. In other embodiments the hydrogenation catalyst is removed using centrifugation followed by decantation of the product.

Emollient

The liquid composition may include an emollient. Emollients may (1) hydrate the residues (for example, fecal residues or dried urine residues or menses), thus enhancing their removal from the skin, (2) hydrate and lubricate the skin, thus reducing its dryness and irritation while improving its flexibility under the wiping movement, (3) reduce the adhesive interaction between the soil and the surface, and (4) protect the skin from later irritation (for example, caused by the friction of an absorbent article or acting as a barrier from irritants present in feces or urine) as the emollient is deposited onto the skin and remains at its surface as a thin protective layer. The emollient may also improve or maintain the integrity of the skin's health as the emollient may deposit beneficial compounds such as essential fatty acids, which are present in certain vegetable oils.

Exemplary emollients include, but are not limited to, vegetable oils such as sunflower seed oil, canola oil, avocado oil, olive oil, emu oil, babassu oil, evening primrose oil, cottonseed oil, jojoba oil, meadowfoam seed oil, sweet almond oil, canola oil, safflower oil, coconut oil, sesame oil, rice bran oil, and grape seed oil; hydrocarbon emollients like mineral oil and petrolatum; esters like isopropyl stearate, isostearyl isononanoate, diethylhexyl fumarate, diisostearyl malate, triisocetyl citrate, stearyl stearate, methyl palmitate, and methylheptyl isostearate; petrolatum; lanolin oil and lanolin wax; long chain alcohols like cetyl alcohol, stearyl alcohol, behenyl alcohol, isostearyl alcohol, 2-hexyldecanol and myristyl alcohol; hydrophilic emollients like glycerin polyglycerols; dimethicone fluids of various molecular weights including dimethicone with a viscosity of 200 centistokes such as Momentive's ELEMENT14™ PDMS-200, or derivatized dimethicones including alkyl dimethicones such as cetyl dimethicone marketed by Dow Corning as DOW CORNING® 2502 Cosmetic Fluid, and mixtures thereof; PPG-15 stearyl ether (also known as arlatone E); vegetable butters such as shea butter, olive butter, sunflower butter, coconut butter, jojoba butter, and cocoa butter; squalane and squalene; and isoparaffins.

Emollients may include high oleic canola Oil (*Brassica campestris, B. napus, B. rapa*), very high oleic canola oil, or partially hydrogenated canola oil, pumpkin seed oil, high oleic safflower oil (*Carthamus Tinctorius*), sesame oil (*Sesamum indicum, S. oreintale*), high oleic soybean oil or partially hydrogenated soybean oil, high oleic sunflower seed oil (*Helianthus annus*) or mid oleic sunflower and mixtures thereof, olive oil, emu oil, babassu oil, evening primrose oil, palm kernel oil, cottonseed oil, jojoba oil, meadowfoam seed oil, sweet almond oil, coconut oil, rice bran oil, and grape seed oil. High oleic canola oil, palm oil, sesame oil, high oleic safflower oil, high oleic soybean oil, mid oleic sunflower seed oil, and high oleic sunflower seed oil are common plant-bred derived oils and may be also be derived from non-genetically modified organisms (non-GMO).

Non-limiting examples of emollients are commercially available from a number of vendors, including Cargill for partially hydrogenated soybean oil (i.e., Preference® 110W Soybean Oil or Preference® 300 Hi Stability Soybean Oil), mid oleic sunflower seed oil (i.e., NuSun® Mid-Oleic Sunflower Oil), high oleic sunflower seed oil (i.e., ClearValley® High Oleic Sunflower Oil or RB Hi-Oleic Sunflower Oil), high oleic canola oil, very high oleic canola, and partially hydrogenated low erucic rapeseed oil (i.e., Clear Valley® 65 High Oleic Canola Oil and Clear Valley® 75 High Oleic Canola Oil); Lambert Technology for high oleic canola oil (i.e., Oleocal C104); Pioneer for high oleic soybean oil (i.e., Plenish®); Asoyia for low linolenic soybean oil (i.e., Ultra Low Linolenic Soybean Oil®); and Dipasa, Inc. for refined sesame oil.

Some lipophilic emollients may also act as a thickener or hardening agent, especially for the oil phase of an emulsion (viscosity-increasing agents, although perhaps not rheology modifiers in the sense of structuring the continuous phase of an oil-in-water emulsion composition). Such thickening emollients include, but are not limited to, hydrogenated vegetable oils like hydrogenated jojoba oil and hydrogenated jojoba wax; coconut oil; ethylene vinyl acetate polymers, microcrystalline wax; paraffin wax; beeswax; carnauba wax; ozokerite wax; ceresine wax; myristyl alcohol; behenyl alcohol; cetyl alcohol; stearyl alcohol; cetearyl alcohol; and mixtures thereof.

In some exemplary configurations, the emollient may be liquid at 25° C., or may be solid at 25° C.

In some exemplary configurations, the aqueous liquid composition may comprise from about 1% to about 5%, or about 2% to about 4%, by weight of the liquid composition, of an emollient, specifically including 0.1% increments within the above-specified range and any ranges within the specified range.

One or more emollients may be present from about 0.01 wt % to about 10 wt %, alternatively from about 0.1 wt % to about 8 wt %, and alternatively from about 0.2 wt % to about 4 wt %, by weight of the composition.

Silicones

Silicones may be used as emollients. The silicone may comprise volatile silicone, non-volatile silicone, or combinations thereof. If volatile silicones are present, it will typically be incidental to their use as a solvent or carrier for commercially available forms of non-volatile silicone materials ingredients, such as silicone gums and resins. The silicone may comprise a silicone fluid and may also comprise other ingredients, such as a silicone resin to improve silicone fluid deposition efficiency or enhance softness of the skin.

The concentration of the silicone typically ranges from about 0.01% to about 10%, by weight of the composition, alternatively from about 0.1% to about 8%, alternatively from about 0.1% to about 5%, and alternatively from about 0.2% to about 3%. Non-limiting examples of suitable silicones, and optional suspending agents for the silicone, are described in U.S. Reissue Pat. No. 34,584, U.S. Pat. Nos. 5,104,646, and 5,106,609. The silicones for use in the wet wipes composition may have a viscosity, as measured at 25° C., from about 20 to about 2,000,000 centistokes ("csk"), alternatively from about 1,000 to about 1,800,000 csk, alternatively from about 50,000 to about 1,500,000 csk, and alternatively from about 100,000 to about 1,500,000 csk.

The silicone may be dispersed as particles in the composition. The dispersed silicone particles typically have a volume average particle diameter ranging from about 0.01 micrometer to about 50 micrometer. For small particle application to skin, the volume average particle diameters typically range from about 0.01 micrometer to about 4 micrometer, alternatively from about 0.01 micrometer to about 2 micrometer, and alternatively from about 0.01 micrometer to about 0.5 micrometer. For larger particle application to skin, the volume average particle diameters typically range from about 5 micrometer to about 125 micrometer, alternatively from about 10 micrometer to about 90 micrometer, alternatively from about 15 micrometer to about 70 micrometer, and alternatively from about 20 micrometer to about 50 micrometer.

Background material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989).

Silicone Oils

Silicone fluids include silicone oils, which are flowable silicone materials having a viscosity, as measured at 25° C., less than 1,000,000 csk, alternatively from about 5 csk to about 1,000,000 csk, and alternatively from about 100 csk to about 600,000 csk. Suitable silicone oils for use in the wet wipes composition include polyalkyl siloxanes, polyaryl siloxanes, polyalkylaryl siloxanes, polyether siloxane copolymers, and mixtures thereof. Other insoluble, non-volatile silicone fluids having skin softening properties may also be used.

Silicone oils include polyalkyl or polyaryl siloxanes which conform to the following Formula (I):

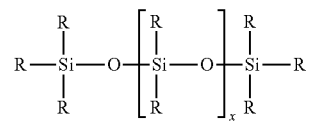

wherein R is aliphatic, in some embodiments alkyl, alkenyl, or aryl, R can be substituted or unsubstituted, and x is an integer from 1 to about 8,000. Suitable R groups for use in the compositions include, but are not limited to: alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

Possible alkyl and alkenyl substituents include $C_1$ to $C_5$ alkyls and alkenyls, alternatively from $C_1$ to $C_4$, and alternatively from $C_1$ to $C_2$. The aliphatic portions of other alkyl-, alkenyl-, or alkynyl-containing groups (such as alkoxy, alkaryl, and alkamino) can be straight or branched chains, and may be from $C_1$ to $C_5$, alternatively from $C_1$ to $C_4$, alternatively from $C_1$ to $C_3$, and alternatively from $C_1$ to $C_2$. As discussed above, the R substituents can also contain amino functionalities (e.g. alkamino groups), which can be primary, secondary or tertiary amines or quaternary ammonium. These include mono-, di- and tri-alkylamino and alkoxyamino groups, wherein the aliphatic portion chain length may be as described herein.

Amino and Cationic Silicones

Silicone fluids include amino and cationic silicones. Cationic silicone fluids suitable for use in the compositions include, but are not limited to, those which conform to the general formula (II):

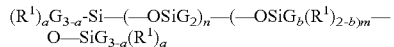

wherein G is hydrogen, phenyl, hydroxy, or $C_1$-$C_8$ alkyl, in some embodiments, methyl; a is 0 or an integer having a value from 1 to 3; b is 0 or 1; n is a number from 0 to 1,999, alternatively from 49 to 499; m is an integer from 1 to 2,000, alternatively from 1 to 10; the sum of n and m is a number from 1 to 2,000, alternatively from 50 to 500; $R^1$ is a monovalent radical conforming to the general formula $C_qH_{2q}L$, wherein q is an integer having a value from 2 to 8 and L is selected from the following groups:

—N($R^2$)$CH_2$—$CH_2$—N($R^2$)$_2$
—N($R^2$)$_2$
—N($R^2$)$_3$A$^-$
—N($R^2$)$CH_2$—$CH_2$—NR$^2$H$_2$A$^-$ wherein $R^2$ is hydrogen, phenyl, benzyl, or a saturated hydrocarbon radical, in some embodiments an alkyl radical from about $C_1$ to about $C_{20}$, and A$^-$ is a halide ion.

In one embodiment, the cationic silicone corresponding to formula (II) is the polymer known as "trimethylsilylamodimethicone", which is shown below in formula (III):

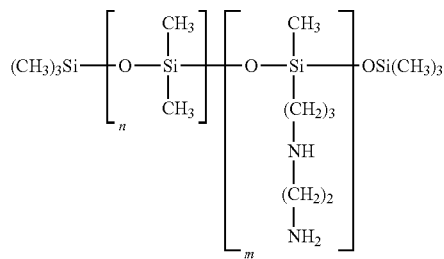

Other silicone cationic polymers which may be used in the wet wipes composition are represented by the general formula (IV):

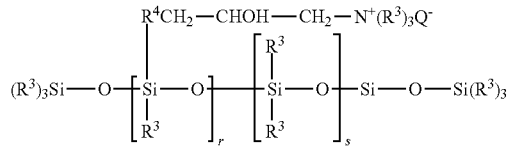

wherein $R^3$ is a monovalent hydrocarbon radical from $C_1$ to $C_{18}$, in some embodiments an alkyl or alkenyl radical, such as methyl; $R_4$ is a hydrocarbon radical, in some embodiments a $C_1$ to $C_{18}$ alkylene radical or a $C_{10}$ to $C_{18}$ alkyleneoxy radical, alternatively a $C_1$ to $C_8$ alkyleneoxy radical; Q$^-$ is a halide ion, in some embodiments chloride; r is an average statistical value from 2 to 20, in some embodiments from 2 to 8; s is an average statistical value from 20 to 200, in some embodiments from 20 to 50. One polymer of this class is known as UCARE SILICONE ALE 56®, available from Union Carbide.

Silicone Gums

Other silicone fluids suitable for use in the wet wipes composition are the insoluble silicone gums. These gums are polyorganosiloxane materials having a viscosity, as measured at 25° C., of greater than or equal to 1,000,000 csk. Silicone gums are described in U.S. Pat. No. 4,152,416; Noll and Walter, Chemistry and Technology of Silicones, New York: Academic Press (1968); and in General Electric Silicone Rubber Product Data Sheets SE 30, SE 33, SE 54 and SE 76. Specific non-limiting examples of silicone gums for use in the skin care include polydimethylsiloxane, (polydimethylsiloxane)(methylvinylsiloxane)copolymer, poly(dimethylsiloxane)(diphenyl siloxane)(methylvinylsiloxane) copolymer and mixtures thereof.

High Refractive Index Silicones

Other non-volatile, insoluble silicone fluid softening agents that are suitable for use in the wet wipes composition are those known as "high refractive index silicones," having a refractive index of at least about 1.46, alternatively at least about 1.48, alternatively at least about 1.52, and alternatively at least about 1.55. The refractive index of the polysiloxane fluid will generally be less than about 1.70, typically less than about 1.60. In this context, polysiloxane "fluid" includes oils as well as gums. The high refractive index polysiloxane fluid includes those represented by general Formula (I) above, as well as cyclic polysiloxanes such as those represented by Formula (V) below:

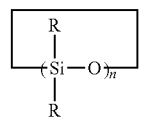

wherein R is as defined above, and n is a number from about 3 to about 7, alternatively from about 3 to about 5.

The high refractive index polysiloxane fluids contain an amount of aryl-containing R substituents sufficient to increase the refractive index to the desired level, which is described herein. Additionally, R and n may be selected so that the material is non-volatile.

Aryl-containing substituents include those which contain alicyclic and heterocyclic five and six member aryl rings and those which contain fused five or six member rings. The aryl rings themselves can be substituted or unsubstituted.

Generally, the high refractive index polysiloxane fluids will have a degree of aryl-containing substituents of at least about 15%, alternatively at least about 20%, alternatively at least about 25%, alternatively at least about 35%, and alternatively at least about 50%. Typically, the degree of aryl substitution will be less than about 90%, more generally less than about 85%, alternatively from about 55% to about 80%. In some embodiments, the high refractive index polysiloxane fluids have a combination of phenyl or phenyl derivative substituents, with alkyl substituents, in some embodiments $C_1$-$C_4$ alkyl, hydroxy, or $C_1$-$C_4$ alkylamino (especially —R$^4$NHR$^5$NH2 wherein each $R^4$ and $R^5$ independently is a $C_1$-$C_3$ alkyl, alkenyl, and/or alkoxy).

When high refractive index silicones are used in the skin care composition, they may be used in solution with a spreading agent, such as a silicone resin or a surfactant, to reduce the surface tension by a sufficient amount to enhance spreading and thereby enhance the glossiness (subsequent to drying) of skin treated with the compositions.

Silicone fluids suitable for use in the wet wipes composition are disclosed in U.S. Pat. Nos. 2,826,551, 3,964,500, 4,364,837, British Pat. No. 849,433, and Silicon Compounds, Petrarch Systems, Inc. (1984).

Silicone Resins

Silicone resins may be included in the silicone of the composition. These resins are highly cross-linked polymeric siloxane systems. The cross-linking is introduced through the incorporation of trifunctional and tetrafunctional silanes with monofunctional or difunctional, or both, silanes during manufacture of the silicone resin.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetrafunctional unit $SiO_2$. Primes of the unit symbols (e.g. M', D', T', and Q') denote substituents other than methyl, and must be specifically defined for each occurrence.

Silicone resins for use in the wet wipes composition may include, but are not limited to MQ, MT, MTQ, MDT and MDTQ resins. Methyl is a possible silicone substituent. In some embodiments, silicone resins are MQ resins, wherein the M:Q ratio is from about 0.5:1.0 to about 1.5:1.0 and the average molecular weight of the silicone resin is from about 1000 to about 10,000.

The weight ratio of the non-volatile silicone fluid, having refractive index below 1.46, to the silicone resin component, when used, may be from about 4:1 to about 400:1, alternatively from about 9:1 to about 200:1, and alternatively from about 19:1 to about 100:1, particularly when the silicone fluid component is a polydimethylsiloxane fluid or a mixture of polydimethylsiloxane fluid and polydimethylsiloxane gum as described herein. Insofar as the silicone resin forms a part of the same phase in the compositions hereof as the silicone fluid, i.e. the softening active, the sum of the fluid and resin should be included in determining the level of silicone softening agent in the composition.

Organic Emollient Oils

The emollient may also comprise at least one organic oil, either alone or in combination with other emollients, such as the silicones described above.

Hydrocarbon Oils

Organic emollient oils include hydrocarbon oils. Suitable organic oils include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils may be from about $C_{12}$ to about $C_{19}$. Branched chain hydrocarbon oils, including hydrocarbon polymers, typically will contain more than 19 carbon atoms.

Polyolefins

Organic emollients for use in the wet wipes composition can also include liquid polyolefins, alternatively liquid poly-α-olefins, alternatively hydrogenated liquid poly-α-olefins. Polyolefins for use herein are prepared by polymerization of $C_4$ to about $C_{14}$ olefenic monomers, in some embodiments from about $C_6$ to about $C_{12}$.

Fatty Esters

Other suitable organic emollient oils include fatty esters having at least 10 carbon atoms. These fatty esters include esters with hydrocarbyl chains derived from fatty acids or alcohols. The hydrocarbyl radicals of the fatty esters hereof may include or have covalently bonded thereto other compatible functionalities, such as amides and alkoxy moieties (e.g., ethoxy or ether linkages, etc.).

Fluorinated Emollient Compounds

Organic emollient oils include fluorinated compounds. Fluorinated compounds suitable for delivering softening and emolliency to the skin as organic softening emollient oils include perfluoropolyethers, perfluorinated olefins, fluorine based specialty polymers that may be in a fluid or elastomer form similar to the silicone fluids previously described, and perfluorinated dimethicones.

Fatty Alcohols

Other suitable organic emollient oils for use in the personal care wet wipes composition include, but are not limited to, fatty alcohols having at least about 10 carbon atoms, alternatively from about 10 to about 22 carbon atoms, and alternatively from about 12 to about 16 carbon atoms. The fatty alcohols can also function as both hardening agents and emollients in the anhydrous compositions of the metathesized polyol esters.

Clay Mineral

The liquid composition may comprise a clay mineral. Surprisingly, it has been found that a liquid composition comprising an emollient and a clay mineral has little to no greasy or slimy feel. As a result, a liquid composition may comprise an emollient to deliver beneficial compounds to the skin, without having a greasy and/or slimy feel from the composition. Furthermore, a liquid composition comprising an emollient and a clay mineral has good long-term stability. Some clay minerals possess multi-functional characteristics in being capable of emulsifying emollients while also increasing the viscosity of the composition. Some clay minerals and derivatized clay minerals are also useful in thickening anhydrous compositions containing the metathesized polyol esters.

Without wishing to be bound by theory, it is believed that the clay mineral can form a hard, solid, and insoluble interfacial film on the surface of the lipophilic emollient droplets in order to inhibit the emollient drops from coalescing. In addition and as noted, it is believed that the network formed between the clay mineral and a rheology modifier like xanthan gum can inhibit the Brownian motion of the lipophilic emollient droplets to further inhibit coalescence. Brownian motion is the random movement of particles suspended in a fluid, including a liquid or a gas, resulting from their bombardment by the fast-moving atoms or molecules in the fluid. Finally, without wishing to be bound by theory, it is believed that the negative charge contributed by the clay mineral adsorption on the surface of the lipophilic emollient droplets causes repulsion between the lipophilic emollient droplets to enhance the stability of the emulsion.

Clay minerals are also believed to have a good safety profile for use on skin of babies. The particle size of many clay minerals is about 1 micron or greater. As a result, clay minerals are not able to penetrate into the skin and cause irritation. Furthermore, clay minerals are inert and do not react to form potential irritating products. Clay minerals also improve the skin mildness of the liquid composition by binding potential irritants such that these irritants are inhibited from causing negative reactions with the skin.

Exemplary clay minerals include smectite clays such as R.T. Vanderbilt's VEEGUM® Ultra or VEEGUM® HS; montmorillonite clays such as MINERAL COLLOID® BP from Southern Clay Products, Inc.; hectorite clays such as HECTABRITE® DP from Amcol Specialty Minerals; kaolinite clays such as Colloidal Kaolin USP/BC from Brenntag Specialties, Inc.; fumed silicas and modified fumed silicas like the Cab-O-Sil® brand from Cabot Corporation;

palygorskite clays such as ATTAGEL® or PHARMASORB® Colloidal from BASF Corporation; sepiolite clays such as Pangel B from Ecolog Materials Group; and saponite clays. In some exemplary configurations, the liquid composition may comprise a modified clay mineral such as modified montmorillonite clay, including CLAYTONE® AF from Southern Clay Products Inc; modified bentonite clay such as CLAYTONE® XL of Southern clay Products, Inc.; and modified hectorite clay such as BENTONE® 27V CG of Elementis Specialities. Exemplary clay minerals may include synthetic clay such as LAPONITE® clay. An exemplary LAPONITE® clay is LAPONITE® XLG from Southern Clay Products, Inc.

In order to minimize the greasy and/or slimy feel of the liquid composition, the weight ratio of emollient to clay mineral present in the liquid composition may be about 1:1 to about 30:1, or about 5:1 to about 20:1. In some exemplary configurations, the liquid composition may comprise from about 0.1% to about 5.0%, by weight of the liquid composition, of clay mineral.

Rheology Modifier

Non-limiting examples of rheology modifiers include the clay minerals described above and rheology modifiers comprising: polysaccharide units, e.g. cellulose, xanthan gum, diutan gum, guar gum, dextran gum, locust bean gum, carrageenan, gellan gum, konjac gum, welan gum, pectin, sclerotium gum, welan gum, starch, galactoarabinan, alginate, and modified-forms thereof; homopolymers of acrylic acid; acrylic acid cross-linked with a polyfunctional compound, e.g. carbomer and acrylate crosspolymer; copolymers of acrylic acid, acrylate esters, maleic acid and the like, generally known as the alkali swellable emulsions (ASE) group; hydrophobically-modified copolymers of acrylic acid, acrylate esters, maleic acid and the like, generally known as the hydrophobically-modified alkali swellable emulsions (HASE) group; polyethylene glycol units of varying length connected by urethane linkages and terminated with hydrophobic end groups, generally known as the hydrophobically-modified ethoxylated urethane resins (HEUR) group; organoclays; silicas; fumed silicas and modified fumed silicas; and combinations thereof.

In some exemplary configurations, the liquid composition may comprise an emollient, a clay mineral, emulsifier, and xanthan gum.

In some exemplary configurations, the liquid composition may comprise from about 0.05% to about 0.2%, by weight of the liquid composition, of a rheology modifier. In order to minimize the greasy and/or slimy feel of the liquid composition, the weight ratio of clay mineral to rheology modifier present in the liquid composition may be about 1:2 to about 16:1, or about 1:1 to about 5:1.

The weight ratio of emollient to rheology modifier present in the liquid composition may be about 5:1 to about 60:1, or about 10:1 to about 30:1.

The weight ratio of emollient to the sum of the clay mineral in combination with the rheology modifier present in the liquid composition may be about 1:1 to about 20:1, or about 5:1 to about 10:1.

Emulsifier

The liquid composition may include one or more emulsifiers. The emulsifier can be an individual emulsifier or a mixture of emulsifiers. The emulsifier may be a polymeric emulsifier or a non-polymeric one. The emulsifier may be nonionic, anionic, cationic, amphoteric or zwetterionic in nature. As noted, some of the clay minerals can also function as emulsifiers.

Various emulsifiers may be used, including those selected from the group consisting of: nonionic emulsifiers, anionic emulsifiers, cationic emulsifiers, amphoteric emulsifiers, zwitterionic emulsifiers, and mixtures thereof. In some exemplary configurations, nonionic emulsifiers may be chosen, at least in part, for skin mildness properties.

In some exemplary configurations, emulsifiers may be selected from the group consisting of: monoacylglycerides and diacylglycerides, also known as monoglycerides and diglycerides, including glycerol monostearate and DIMODAN® C/B K-A, which is a monoglyceride made from cottonseed oil that is manufactured by DUPONT™ DANISCO®; propylene glycol esters of fatty acids; polyglycerol esters of fatty acids, including decaglyceryl monostearate such as POLYALDO® 10-1-S manufactured by Lonza Group Ltd.; sorbitan fatty acid esters, including sorbitan monostearate such as SPAN™ 60 manufactured by Croda International Plc., and sorbitan trioleate such as SPAN™ 85 manufactured by Croda International Plc.; polyoxyethylene derivatives of sorbitan fatty acid esters, also known as polysorbates or polyoxyethylene sorbitan esters, including polyoxyethylene 20 sorbitan monostearate such as TWEEN® 60 manufactured by Croda International Plc.; sucrose esters, including sucrose cocoate and SUCROSILK® HP10 manufactured by Sisterna and SISTERNA® SP70 manufactured by Sisterna; sodium and calcium stearoyl lactylate; derivatives of monoacylglycerols and diacylglycerols, including acetylated mono- and diacylglycerols, lactylated mono- and diacylglycerols, succinylated mono- and diacylglycerols, citrate esters of mono- and diacylglycerols such as glyceryl stearate citrate sold under the designation IMWITOR® 372P(V) by Peter Cremer Incorporated, diacetyl tartaric acid esters of mono- and diacylglycerol, mono- and diacylglycerol phosphates, ethoxylated mono- and diacylglycerols; lecithins and modified lecithins; propylene glycol alginate; alkyl esters of cellulose; fatty acids, including stearic acid and oleic acid; fatty acid soaps, including sodium stearate, which is sold under the designation OP™-100V by Hallstar Incorporated; fatty alcohols, including cetyl alcohol, stearyl alcohol, and cetearyl alcohol such as TA-1618 from Procter & Gamble Chemicals; polyoxyethylene fatty ether emulsifiers like the BRU® brand from Croda International Plc.; polyoxyethylene fatty acid esters like the MYRJ® brand from Croda International Plc.; self emulsifying (SE) emulsifiers, including ARLACEL® 165 from Croda International Plc. which is a mixture of glycerol monostearate and polyoxyethylene stearate, IMWITOR® 960 K from Peter Cremer Incorporated, which is self emulsifying glyceryl stearate with a monoester content of approximately 30%, and ALDO® MSD KFG of Lonza Inc, which is also a self emulsifying glyceryl stearate; and combinations thereof.

Other non-ionic emulsifiers include polyoxyethylene fatty glycerides such as polyoxyethylene 25 hydrogenated castor oil sold under the designation ARLATONE® G by Croda International Plc., polyoxyethylene 40 hydrogenated castor oil sold under the designation EMULSOGEN® hcw-049 by Clariant Inc., polyoxyethylene fatty acid esters such as polyoxyethylene 8 stearate sold under the designation MYRJ® 45 by Croda International Plc.; polyoxyethylene polyol fatty acid esters; polyoxyethylene fatty ethers, including polyoxyethylene 2 stearyl ether, polyoxyethylene 10 stearyl ether, and polyoxyethylene 20 stearyl ether all offered for sale by Croda International Plc.

Other emulsifiers include phosphate esters such as monostearyl phosphate and citrate esters such as monocetyl citrate. Alkyl glucosides are also suitable emulsifiers with examples being coco-glucoside sold under the designation PLANTA-CARE® 818UP by Cognis International Plc. and decyl glucoside sold under the designation PLANTAREN® 2000 N UP by Cognis International Plc. Other exemplary emulsifiers may be selected from the group consisting of: alkyl polyglucosides, polyhydroxy fatty acid amides, cocoaamphoacetate, cocoamphodiacetate, lauroamphoacetate, lauroamphodiacetate, betaines and derivatized betaines, sultaines and derivatized sultaines, and mixtures thereof.

In some exemplary configurations, the emulsifier may include sodium stearate. In some exemplary configurations, the liquid composition may comprise glycerol stearate citrate. In other exemplary configurations, the liquid composition may comprise both sodium stearate and glycerol stearate citrate.

The liquid composition may comprise a single emulsifier, or may comprise more than one emulsifier.

The emulsifier, when present in the liquid composition, may be present in an amount ranging from about 0.0% to about 10%, or about 0.1% to about 5%, or about 0.3% to about 3% by weight of the liquid composition.

Emulsifiers that have an alkyl chain of C16 or longer having a similar structure to lipids comprising biological membranes may be particularly well suited for the liquid composition of the present disclosure.

Preservative

Controlling microbiological growth may be beneficial in water based products such as liquid compositions intended for use in wet wipes.

The spectrum of activity of the preservative may include bacteria, molds and yeast. Each of such microorganisms may be killed by the preservative. Another mode of action to be contemplated may be the reduction of the growth rate of the microorganisms without active killing. Both actions however result in a drastic reduction of the population of microorganisms.

Materials useful as preservatives include methylol compounds, iodopropynyl compounds, simple aromatic alcohols, paraben compounds, benzyl alcohol, benzoic acid, benzoates, sorbic acid, sorbates, phenoxyethanol, ethxylhexyglycerin, chelators such as ethylenediamine tetraacetic acid, and combinations thereof. Suitable preservative systems are described in U.S. Patent Publication No. 2005/0008680 and U.S. Patent Publication No. 2005/0008681.

Low pH buffering systems, such as a citrate-citric acid buffering system at a pH of less than about 4.5, may also be employed as part of the preservative system.

In some exemplary configurations, the preservative system may comprise simple aromatic alcohols (e.g. benzyl alcohol). Materials of this type may have effective antibacterial activity. Benzyl alcohol is available from Symrise, Inc. of Teterboro, N.J. In other exemplary configurations, the preservative system may comprise a mixture of benzyl alcohol, sodium benzoate, phenoxyethanol, ethylhexylglycerin, ethylenediamine tetraacetic acid, citric acid, and sodium citrate dehydrate wherein the pH of the liquid composition is less than about 4. The total concentration of benzyl alcohol may be lower than about 0.4% by weight of the liquid composition. The total concentration of sodium benzoate may be lower than about 0.3% by weight of the liquid composition. The combination of phenoxyethanol and ethylhexylglycerin, which are available as EUXYL® PE 9010 from Schulke & Mayr GmbH of Germany, may be lower than about 0.4%.

In some exemplary configurations, acidic compounds used in sufficient amount to reduce the pH of the liquid composition (e.g. pH of less than about 5) may be useful as the preservative, or as a potentiator for other preservative ingredients. The preservative system of the lotion emulsion composition may include additional compounds, for example chelating agents, such as ethylenediamine tetraacetic acid (EDTA) and its salts, or diethylene triamine pentaacetic acid (DTPA).

In some exemplary configurations, acidic compounds used in sufficient amount to reduce the pH of the lotion emulsion composition (e.g. pH of less than about 5) may be useful as a part of the preservative system. Low pH buffering systems, such as a citrate-citric acid buffering system, such as trisodium citrate and citric acid, at a pH of less than about 5, or less than about 4, may be employed as part of the preservative system.

The preservative system of the lotion emulsion composition may comprise one or more preservative enhancing agents in combination with one or more preservatives. It has been found that a wet wipe having a lotion emulsion composition comprising a preservative enhancing agent and a preservative may have improved antimicrobial performance compared to a wet wipe having a lotion emulsion composition comprising a preservative without a preservative enhancing agent. As a result, lower concentrations of a preservative may be used in a lotion emulsion composition comprising a preservative enhancing agent than may be used when the lotion emulsion composition comprises a preservative without a preservative enhancing agent.

An exemplary wet wipe may include a lotion emulsion composition comprising a preservative enhancing agent and a preservative. In an exemplary configuration, the lotion emulsion composition may comprise sorbitan caprylate and/or glyceryl caprylate/caprate and sodium benzoate. In a further exemplary configuration, the lotion emulsion composition may comprise sorbitan caprylate and/or glyceryl caprylate/caprate, sodium benzoate, EDTA, and a citrate-citric acid buffering system at a pH of less than about 4. Suitable preservatives and preservative system materials may be such as disclosed in U.S. Ser. Nos. 14/867,059 and 14/330,171. The lotion emulsion composition may include one or more preservatives. The preservative may include an organic acid or the salt thereof. Exemplary organic acids include benzoic acid or sorbic acid. Exemplary salts of organic acids include sodium benzoate and potassium sorbate, for example.

The preservative may be present in an amount ranging from about 0.1% to about 4%, or about 0.3% to about 2%, or about 0.5% to about 1% by weight of the liquid composition.

Perfumes/Fragrances

The perfumes and compositions of this invention are the conventional ones known in the art. Selection of any perfume component, or amount of perfume, is based on functional and aesthetic considerations. Preferred perfume components useful in the present invention are the highly volatile, and the moderately volatile perfume ingredients, more preferably the highly volatile, low boiling perfumes.

The highly volatile, low boiling, perfume ingredients typically have boiling points of about 250° C. or lower. These highly volatile perfumes are fleeting and are quickly lost as they are released. Many of the more moderately volatile perfume ingredients are also quickly lost. The moderately volatile perfume ingredients are those having boiling points of from about 250° C. to about 300° C. Many of the perfume ingredients as discussed hereinafter, along with their odor characters, and their physical and chemical properties, such as boiling point and molecular weight, are given in "Perfume and Flavor Chemicals (Aroma Chemicals)," Steffen Arctander, published by the author, 1969, incorporated herein by reference.

Examples of the highly volatile, low boiling, perfume ingredients are: anethole, benzaldehyde, benzyl acetate, benzyl alcohol, benzyl formate, iso-bornyl acetate, camphene, cis-citral (neral), citronellal, citronellol, citronellyl acetate, para-cymene, decanal, dihydrolinalool, dihydromyrcenol, dimethyl phenyl carbinol, eucalyptol, geranial, geraniol, geranyl acetate, geranyl nitrile, cis-3-hexenyl acetate, hydroxycitronellal, d-limonene, linalool, linalool oxide, linalyl acetate, linalyl propionate, methyl anthranilate, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, phenyl ethyl alcohol, alpha-pinene, beta-pinene, gamma-terpinene, alpha-terpineol, beta-terpineol, terpinyl acetate, and vertenex (para-tertiary-butyl) cyclohexyl acetate). Some natural oils also contain large percentages of highly volatile perfume ingredients. For example, lavandin contains as major components: linalool; linalyl acetate; geraniol; and citronellol. Lemon oil and orange terpenes both contain about 95% of d-limonene.

Examples of moderately volatile perfume ingredients are: amyl cinnamic aldehyde, iso-amyl salicylate, beta-caryophyllene, cedrene, cinnamic alcohol, coumarin, dimethyl benzyl carbinyl acetate, ethyl vanillin, eugenol, iso-eugenol, flor acetate, heliotropine, 3-cis-hexenyl salicylate, hexyl salicylate, lilial (para-tertiarybutyl-alpha-methyl hydrocinnamic aldehyde), gamma-methyl ionone, nerolidol, patchouli alcohol, phenyl hexanol, beta-selinene, trichloromethyl phenyl carbinyl acetate, triethyl citrate, vanillin, and veratraldehyde. Cedarwood terpenes are composed mainly of alpha-cedrene, beta-cedrene, and other $C_{15}H_{24}$ sesquiterpenes.

Other odor controlling organic compounds which can be used herein include particular other fragrance/masking/reacting components selected from the lists (c), (d) and (e).

Components from list (c) are menthol, menthyl acetate, menthyl lactate, menthyl propionate, menthyl butyrrate, menthone, mint terpenes, laevo-carvone, Cis-3-Hexenol & Cis-3-Hexenyl acetate, koavone, methyl dioxolan, ethylene brassylate, and salycilate esters. Salycilate esters are preferably selected from amyl salicylate, isoamyl salicylate, isobutyl salicylate, cis-3-hexenyl salicylate, hexyl salicylate, cyclohexyl salicylate, benzyl salicylate, phenylethyl salicylate, propyl salicylate, isopropyl salicylate or mixtures thereof.

These are all compounds which primary function is to mask malodors. This may occur through vapor pressure suppression of the malodor or by overwhelming the unpleasant malodor with the pleasant odor of the fragrance component. These materials, when used, may significantly reduce the ability to detect the malodors. The masking ability to hide malodors is possible due to the volatile nature of the materials selected, which are released from the complex in the absorbent article and are then inhaled into the nose of a consumer, generally within somewhat close range of the absorbent article, e.g. within about 0 to 10 meters of the article by normal breathing (although this should in no way be intended to limit the scope of the invention).

Components from list (d) are methyl-dihydrojasmonate, methyl jasmonate, eucalyptol, tetrahydro-linalool, phenylethyl alcohol, hexyl iso-butyrate, linalyl acetate, benzyl acetate, Benzyl alcohol, or mixture thereof. These are volatile materials which are well complexed with cyclodextrin and are released very quickly upon contact with a water based liquid. Their presence allows the absorbent article to respond even more quickly to an insult of malodorant liquid by releasing a compound that have a good general masking effect against malodors, in particular, being very volatile, reduces the vapor pressure of other malodorant compounds slowing down their evaporation rate.

List (e) includes other malodor masking and fragrance components which can be used as odor controlling organic compounds in the present invention:

e) camphor, p-menthane, limonene, cresol, linalool, myrcenol, tetra hydromyrcenol, di-hydromyrcenol, myrcene, citronellol, citronellyil derivatives, geraniol, geranyl derivatives, mugetanol, eugenol, jasmal, terpineol, pinanol, cedrene, damascone, beta pinene, cineole and its derivatives, nonadienol, ethylhexanal, octanol acetate, methyl furfural, terpinene, thujene, amylacetate, camphene, citronellal, hydroxycitronellal, ethyl maltol, methyl phenyl carbinyl acetate, dihydrocumarin, di-hydromyrcenyl acetate, geraniol, geranial, isoamylacetate, ethyl, and/or triethyl acetate, para-cresol, para-cymene, methyl abietate, hexyl-2-methyl butyrate, hexyl-2-methyl butyrate, and mixtures thereof.

The optional perfume component may comprise a component selected from the group consisting of
(1) a perfume microcapsule, or a moisture-activated perfume microcapsule, comprising a perfume carrier and an encapsulated perfume composition, wherein said perfume carrier may be selected from the group consisting of cyclodextrins, starch microcapsules, porous carrier microcapsules, and mixtures thereof; and wherein said encapsulated perfume composition may comprise low volatile perfume ingredients, high volatile perfume ingredients, and mixtures thereof;
(2) a pro-perfume;
(3) a low odor detection threshold perfume ingredients, wherein said low odor detection threshold perfume ingredients may comprise less than about 25%, by weight of the total neat perfume composition; and
(4) mixtures thereof; and Other Adjunct Ingredients The liquid composition may optionally include other adjunct ingredients. Possible adjunct ingredients may be selected from a wide range of additional ingredients such as texturizers, colorants, soothing agents, anti-oxidants and medically active ingredients, such as healing actives and skin protectants. Non-limiting examples of suitable antioxidants include Vitamin E (tocopherol, including α-tocopherol, β-tocopherol, γ-tocopherol, and δ-tocopherol), tocotrienol, rosemary, oil of rosemary, ascorbic acid, sesamol, sesamolin, sesamin, catechin, citric acid, tocopherol acetate, naringenin, and mixtures thereof.

Wipes

The fibrous structure, as described above, may be utilized to form a wipe. "Wipe" may be a general term to describe a piece of material, generally non-woven material, used in cleansing hard surfaces, food, inanimate objects, toys and body parts. In particular, many currently available wipes may be intended for the cleansing of the perianal area after defecation. Other wipes may be available for the cleansing of the face or other body parts. Multiple wipes may be attached together by any suitable method to form a mitt.

The material from which a wipe is made should be strong enough to resist tearing during normal use, yet still provide softness to the user's skin, such as a child's tender skin. Additionally, the material should be at least capable of retaining its form for the duration of the user's cleansing experience.

Wipes may be generally of sufficient dimension to allow for convenient handling. Typically, the wipe may be cut and/or folded to such dimensions as part of the manufacturing process. In some instances, the wipe may be cut into individual portions so as to provide separate wipes which are often stacked and interleaved in consumer packaging. In other exemplary configurations, the wipes may be in a web form where the web has been slit and folded to a predetermined width and provided with means (e.g., perforations) to allow individual wipes to be separated from the web by a user. Suitably, an individual wipe may have a length between about 100 mm and about 250 mm and a width between about 140 mm and about 250 mm. In one exemplary configuration, the wipe may be about 200 mm long and about 180 mm wide and/or about 180 mm long and about 180 mm wide and/or about 170 mm long and about 180 mm wide and/or about 160 mm long and about 175 mm wide. The material of the wipe may generally be soft and flexible, potentially having a structured surface to enhance its cleaning performance.

It is also within the scope of the present disclosure that the wipe may be a laminate of two or more materials. Commercially available laminates, or purposely built laminates would be within the scope of the present disclosure. The laminated materials may be joined or bonded together in any suitable fashion, such as, but not limited to, ultrasonic bonding, adhesive, glue, fusion bonding, heat bonding, thermal bonding and combinations thereof. In another alternative exemplary configuration of the present disclosure the wipe may be a laminate comprising one or more layers of nonwoven materials and one or more layers of film. Examples of such optional films, include, but are not limited to, polyolefin films, such as, polyethylene film. An illustrative, but non-limiting example of a nonwoven material which is a laminate is a laminate of a 16 gsm nonwoven polypropylene and a 0.8 mm 20 gsm polyethylene film.

The wipes may also be treated to improve the softness and texture thereof by processes such as hydroentanglement or spunlacing. The wipes may be subjected to various treatments, such as, but not limited to, physical treatment, such as ring rolling, as described in U.S. Pat. No. 5,143,679; structural elongation, as described in U.S. Pat. No. 5,518,801; consolidation, as described in U.S. Pat. Nos. 5,914,084, 6,114,263, 6,129,801 and 6,383,431; stretch aperturing, as described in U.S. Pat. Nos. 5,628,097, 5,658,639 and 5,916,661; differential elongation, as described in WO Publication No. 2003/0028165A1; and other solid state formation technologies as described in U.S. Publication No. 2004/0131820A1 and U.S. Publication No. 2004/0265534A1 and zone activation and the like; chemical treatment, such as, but not limited to, rendering part or all of the fibrous structure hydrophobic, and/or hydrophilic, and the like; thermal treatment, such as, but not limited to, softening of fibers by heating, thermal bonding and the like; and combinations thereof.

The wipe may have a basis weight of at least about 30 grams/m$^2$ and/or at least about 35 grams/m$^2$ and/or at least about 40 grams/m$^2$. In one example, the wipe may have a basis weight of at least about 45 grams/m$^2$. In another example, the wipe basis weight may be less than about 100 grams/m$^2$. In another example, wipes may have a basis weight between about 45 grams/m$^2$ and about 75 grams/m$^2$, and in yet another exemplary configuration a basis weight between about 45 grams/m$^2$ and about 65 grams/m$^2$.

In one example of the present disclosure the surface of wipe may be essentially flat. In another example of the present disclosure the surface of the wipe may optionally contain raised and/or lowered portions. These can be in the form of logos, indicia, trademarks, geometric patterns, images of the surfaces that the fibrous structure is intended to clean (i.e., infant's body, face, etc.). They may be randomly arranged on the surface of the wipe or be in a repetitive pattern of some form.

In another example of the present disclosure the wipe may be biodegradable. For example the wipe could be made from a biodegradable material such as a polyesteramide, or high wet strength cellulose.

In one example of the present disclosure, the fibrous structure is combined with a liquid composition to form a wet wipe, such as a baby wipe. A plurality of the wet wipes may be stacked one on top of the other and may be contained in a container, such as a plastic tub or a film wrapper. In one example, the stack of wet wipes (typically about 40 to 80 wipes/stack) may exhibit a height of from about 50 to about 300 mm and/or from about 75 to about 125 mm. The wet wipes may comprise a liquid composition. The wet wipes may be stored long term in a stack in a liquid impervious container or film pouch without all of the lotion draining from the top of the stack to the bottom of the stack.

In another example, the wet wipes may exhibit a saturation loading (g liquid composition to g of dry wipe) of from about 1.5 to about 6.0 g/g. The liquid composition may exhibit a surface tension of from about 20 to about 35 and/or from about 28 to about 32 dynes/cm.

In one example, the wet wipes are present in a stack of wet wipes that exhibits a height of from about 50 to about 300 mm and/or from about 75 to about 200 mm and/or from about 75 to about 125 mm, wherein the stack of wet wipes exhibits a saturation gradient index of from about 1.0 to about 2.0 and/or from about 1.0 to about 1.7 and/or from about 1.0 to about 1.5.

The fibrous structures or wipes of the present disclosure may be saturation loaded with a liquid composition to form a wet fibrous structure or wipe. The loading may occur individually, or after the fibrous structures or wipes are place in a stack, such as within a liquid impervious container or packet. In one example, the wet wipes may be saturation loaded with from about 150% to about 600% and/or from about 250% g to about 400% of liquid composition per g of wipe.

The fibrous structures or wipes of the present disclosure may be placed in the interior of a container, which may be liquid impervious, such as a plastic tub or a sealable packet, for storage and eventual sale to the consumer. The wipes may be folded and stacked. The wipes of the present disclosure may be folded in any of various known folding patterns, such as C-folding, Z-folding and quarter-folding. Use of a Z-fold pattern may enable a folded stack of wipes to be interleaved with overlapping portions. Alternatively, the wipes may include a continuous strip of material which has perforations between each wipe and which may be arranged in a stack or wound into a roll for dispensing, one after the other, from a container, which may be liquid impervious.

The fibrous structures or wipes of the present disclosure may further comprise prints, which may provide aesthetic appeal. Non-limiting examples of prints include figures, patterns, letters, pictures and combinations thereof.

Exemplary fibrous structures are described in U.S. Patent Application Publication No. 2011/0244199.

TEST METHODS

Molecular Weight Distribution

The weight average molecular weight (Mw) is measured using gel permeation chromatography (GPC) and multi-angle laser light scattering (MALLS). The GPC/MALLS system used for the analysis is comprised of a Waters Alliance e2695 Separations Module, a Waters 2414 interferometric refractometer, and a Wyatt Heleos II 18 angle laser light scattering detector. The column set used for separation is purchased from TOSOH Biosciences LLC, King of Prussia, Pa. and included: Guard Column TSKgel G1000Hx-GMHxl-L (Cat #07113), TSKgel G3000Hx1 (Cat #0016136), TSKgel G2500Hx1 (Cat #0016135), and TSKgel G2000Hx1 (Cat #0016134). Wyatt ASTRA 6 software was used for instrument operation and data analysis. The 90 degree light scattering detection angle is calibrated using filtered, anhydrous toluene. The remaining detection angles are normalized using an isotropic scatterer in THF. To verify instrument performance of the MALLS and RI (refractive index) detectors, a poly(styrene) standard with a known Mw and known dn/dc (in the mobile phase) is run. Acceptable performance of the MALLS and RI detectors gives a calculated Mw within 5% of the reported Mw of the poly (styrene) standard and a mass recovery between 95 and 105%.

To complete the GPC/MALLS analysis, a value of dn/dc is needed. The value of dn/dc is measured as follows. The RI detector is thermostated to 35 degrees Celsius. A series of five concentration standards of the metathesized unsaturated polyol ester in THF is prepared in the range 0.5 mg/ml to 5.5 mg/ml. A THF blank is injected directly into the refractive index detector, followed by each of the metathesized unsaturated polyol ester concentration standards, and ending with another THF blank. The volume of each sample injected is large enough to obtain a flat plateau region of constant differential refractive index versus time; a value of 1.0 ml is typically used. In the ASTRA software, a baseline is constructed from the initial and final THF injections. For each sample, peak limits are defined and the concentrations entered to calculate dn/dc in the ASTRA software. For the metathesized canola oil of Example 2 in THF, a dn/dc value of 0.072 ml/g is obtained.

For the GPC/MALLS analysis of a metathesized unsaturated polyol ester, a total of three samples are evaluated: the metathesized unsaturated polyol ester, a non-metathesized unsaturated polyol ester (glycerol trioleate [122-32-7], Sigma-Aldrich, Milwaukee, Wis.), and a representative olefin (1-octadecene, [112-88-9], Sigma-Aldrich, Milwaukee, Wis.). The GPC samples are dissolved in tetrahydrofuran (THF). Concentrations for the metathesized unsaturated polyol ester are approximately 20 mg/ml, and concentrations for the non-metathesized unsaturated polyol ester and olefin are approximately 5 mg/ml. After all the material is dissolved, each solution is filtered by a 0.45 micron nylon filter disk into a GPC autosampler vial for analysis. The GPC column temperature is at room temperature, approximately 25 degrees Celsius. HPLC grade THF is used as the mobile phase and is delivered at a constant flow rate of 1.0 ml/min. The injection volume is 100 microliters and the run time is 40 minutes. Baselines are constructed for all signals. Peak elution limits include metathesized unsaturated polyol ester and non-metathesized unsaturated polyol ester, but exclude later eluting residual olefin. The retention times of the non-metathesized unsaturated polyol ester and olefin were determined from the separate injection runs of both the non-metathesized unsaturated polyol ester and olefin. Baselines and scattering detectors are reviewed.

Oligomer Index

The oligomer index of the metathesized unsaturated polyol ester is calculated from data that is determined by Supercritical Fluid Chromatography-Fourier Transform Orbital Trapping Mass Spectrometry (SFC-Orbitrap MS). The sample to be analyzed is typically dissolved in methylene chloride or a methylene chloride-hexane mixture at a concentration of 1000 ppm (1 mg/mL). A further 25×-100× dilution is typically made into hexane (for a final concentration of 10-40 ppm). A volume of 2-7.5 μL is typically injected on to a SFC column (for example, a commercially available 3 mm i.d.×150 mm Ethylpyridine column, 3 μM particle size).

During the chromatography run, the mobile phase is typically programmed from 100% carbon dioxide with a gradient of one percent per minute methanol. The effluent from the column is directed to a mixing tee where an ionization solution is added. The ionization medium is typically 20 mM ammonium formate in methanol at a flow of 0.7 mL/min while the SFC flow is typically 1.6 mL/min into the tee. The effluent from the mixing tee enters the ionization source of the Orbitrap Mass Spectrometer, which is operated in the heated electrospray ionization mode at 320° C.

In one aspect, a hybrid linear ion trap—Orbitrap mass spectrometer (i.e., the Orbitrap Elite from Thermoelectron Corp.) is calibrated and tuned according to the manufacturer's guidelines. A mass resolution (m/Δm peak width at half height) from 100,000 to 250,000 is typically used. C,H,O compositions of eluting species (typically associated with various cations, e.g., $NH_4^+$, $H^+$, $Na^+$) are obtained by accurate mass measurement (0.1-2 ppm) and are correlated to metathesis products. Also, sub-structures may be probed by linear ion trap "MS" experiments with subsequent accurate-mass analysis in the Orbitrap, as practiced typically in the art.

The metathesis monomers, dimers, trimers, tetramers, pentamers, and higher order oligomers are fully separated by SFC. The chromatogram based on ion current from the Orbitrap MS may be integrated, as typically practiced in the art, for each of the particular oligomer groups including metathesis monomers, metathesis dimers, metathesis trimers, metathesis pentamers, and each of the higher order oligomers. These raw areas may then be formulated into various relative expressions, based on normalization to 100%. The sum of the areas of metathesis trimers through the highest oligomer detected is divided by the sum of all metathesis species detected (metathesis monomers to the highest oligomer detected). This ratio is called the oligomer index. As used herein, the "oligomer index" is a relative measure of the fraction of the metathesized unsaturated polyol ester which is comprised of trimers, tetramers, pentamers, and higher order oligomers.

Iodine Value

Another aspect of the invention provides a method to measure the iodine value of the metathesized unsaturated polyol ester. The iodine value is determined using AOCS Official Method Cd 1-25 with the following modifications: carbon tetrachloride solvent is replaced with chloroform (25 ml), an accuracy check sample (oleic acid 99%, Sigma-Aldrich; IV=89.86±2.00 cg/g) is added to the sample set, and the reported IV is corrected for minor contribution from olefins identified when determining the free hydrocarbon content of the metathesized unsaturated polyol ester.

Free Hydrocarbon Content

Another aspect of this invention provides a method to determine the free hydrocarbon content of the metathesized unsaturated polyol ester. The method combines gas chromatography/mass spectroscopy (GC/MS) to confirm identity of the free hydrocarbon homologs and gas chromatography with flame ionization detection (GC/FID) to quantify the free hydrocarbon present.

Sample Prep: The sample to be analyzed was typically trans-esterified by diluting (e.g. 400:1) in methanolic KOH (e.g. 0.1N) and heating in a closed container until the reaction was complete (i.e. 90° C. for 30 min.) then cooled to room temperature. The sample solution could then be treated with 15% boron tri-fluoride in methanol and again heated in a closed vessel until the reaction was complete (i.e. at 60° C. for 30 min.) both to acidify (methyl orange—red) and to methylate any free acid present in the sample. After allowing to cool to room temperature, the reaction was quenched by addition of saturated NaCl in water. An organic extraction solvent such as cyclohexane containing a known level internal standard (e.g. 150 ppm dimethyl adipate) was then added to the vial and mixed well. After the layers separated, a portion of the organic phase was transferred to a vial suitable for injection to the gas chromatograph. This sample extraction solution was analyzed by GC/MS to confirm identification of peaks matching hydrocarbon retention times by comparing to reference spectra and then by GC/FID to calculate concentration of hydrocarbons by comparison to standard FID response factors.

A hydrocarbon standard of known concentrations, such as 50 ppm each, of typically observed hydrocarbon compounds (i.e. 1-dodecene, 1-tridecene, 1-tetradecene, 1-pentadecene, 1-hexadecene, 1-heptadecene, 1-octadecene, dodecane, tridecane, tetradecane, pentadecane, hexadecane, heptadecane and octadecane) was prepared by dilution in the same solvent containing internal standard as was used to extract the sample reaction mixture. This hydrocarbon standard was analyzed by GC/MS to generate retention times and reference spectra and then by GC/FID to generate retention times and response factors.

GC/MS: An Agilent 7890 GC equipped with a split/splitless injection port coupled with a Waters QuattroMicroGC mass spectrometer set up in EI+ ionization mode was used to carry out qualitative identification of peaks observed. A non-polar DB1-HT column (15 m×0.25 mm×0.1 um df) was installed with 1.4 mL/min helium carrier gas. In separate runs, 1 uL of the hydrocarbon standard and sample extract solution were injected to a 300° injection port with a split ratio of 25:1. The oven was held at 40° C. for 1 minute then ramped 15 C.°/minute to a final temperature of 325° C. which was held for 10 minutes resulting in a total run time of 30 minutes. The transfer line was kept at 330° C. and the temperature of the EI source was 230° C. The ionization energy was set at 70 eV and the scan range was 35-550 m/z.

GC/FID: An Agilent 7890 GC equipped with a split/splitless injection port and a flame ionization detector was used for quantitative analyses. A non-polar DB1-HT column (5 m×0.25 mm×0.1 um df) was installed with 1.4 mL/min helium carrier gas. In separate runs, 1 uL of the hydrocarbon standard and sample extract solution was injected to a 330° injection port with a split ratio of 100:1. The oven was held at 40° C. for 0.5 minutes then ramped at 40 C.°/minute to a final temperature of 380° C. which was held for 3 minutes resulting in a total run time of 12 minutes. The FID was kept at 380° C. with 40 mL/minute hydrogen gas flow and 450 mL/min air flow. Make up gas was helium at 25 mL/min. The hydrocarbon standard was used to create a calibration table in the Chemstation Data Analysis software including known concentrations to generate response factors. These response factors were applied to the corresponding peaks in the sample chromatogram to calculate total amount of free hydrocarbon found in each sample.

EXAMPLES

Example 1: Synthesis of Metathesized Canola Oil

Prior to the metathesis reaction, the RBD (refined, bleached, and deodorized) canola oil is pre-treated by mixing the oil with 2% (by weight) bleaching clay (Filtrol F-160, BASF, Florham Park, N.J.) and heating to 120° C. with a nitrogen sweep for 1.5 hours. The oil is cooled to room temperature, filtered through a bed of Celite® 545 diatomaceous earth (EMD, Billerica, Mass.), and stored under inert gas until ready to use.

To a round-bottomed flask, the oil is added and sub-surface sparged with inert gas while mixing and heating to 55° C. The catalyst is dissolved in 1,2-dichloroethane ([107-06-2], EMD, Billerica, Mass.) that is stored over 4 Å molecular sieves and sub-surface sparged with inert gas prior to use. After catalyst addition to the reaction flask, a vacuum is applied to remove volatile olefins that are generated. After ~4 hours reaction time, the vacuum is broken and the metathesized unsaturated polyol ester is cooled to room temperature.

The metathesized canola oil is diluted in hexanes ([110-54-3], EMD, Billerica, Mass.). To the diluted material, 2% bleaching clay (Filtrol F-160, BASF, Florham Park, N.J.) is added and mixed for ~6 hours. The oil is filtered through a bed of Celite® 545 diatomaceous earth. The oil is treated a second time with 2% bleaching clay (Filtrol F-160, BASF, Florham Park, N.J.) for ~6 hours. The oil is filtered through a bed of Celite® 545 diatomaceous earth and then rotary evaporated to concentrate.

The metathesized canola oil is then passed through a wipe film evaporator at 180° C. and <0.5 Torr vacuum to remove olefins up to and including C-18 chain lengths. Representative examples are summarized in the table below.

| Example | Pretreated Canola Oil (g)[a] | Catalyst | Catalyst (g) | Max Temperature (° C.) | Max Vacuum (Torr) |
|---|---|---|---|---|---|
| 1A | 500 | 1[b] | 0.25 | 61 | 7.9 |
| 1B | 500 | 2[c] | 0.25 | 62 | 0.6 |

[a]Canola oil from J. Edwards, Braintree, MA.
[b]Tricyclohexylphosphine [4,5-dimethyl-1,3-bis(2,4,6-trimethylphenyl)imidazol-2-ylidene] [2-thienylmethylene]ruthenium (II) dichloride [1190427-50-9] available as CatMETium RF-3 from Evonik Corporation, Parsippany, NJ.
[c]Tricyclohexylphosphine[1,3-bis(2,4,6-trimethylphenyl)imidazol-2-ylidene][2-thienylmethylene] ruthenium(II) dichloride [1190427-49-6] available as CatMETium RF-2 from Evonik Corporation, Parsippany, NJ.

The samples 1A and 1B are analyzed for weight average molecular weight, iodine value, free hydrocarbon content and oligomer index, using methods described previously, and are found to approximately have the following values:

| Example | Mw (g/mol) | Iodine Value (cg/g) | Free Hydrocarbon content (wt %) | Oligomer Index |
|---|---|---|---|---|
| 1A | 5,400 | 85 | 0.5 | 0.05 |
| 1B | 3,900 | 85 | 0.5 | 0.04 |

Example 2: Remetathesis of Metathesized Unsaturated Polyol Ester

Metathesized canola oil, sufficiently stripped of residual olefins (176.28 g from Example 1A) is blended with pre-treated canola oil (350.96 g, pretreated as described in Example 1) in a round-bottomed flask. The blend is sub-surface sparged with inert gas while mixing and heating to 55° C. The catalyst is dissolved in 1,2-dichloroethane ([107-06-2], EMD, Billerica, Mass.) that is stored over 4 Å molecular sieves and sub-surface sparged with inert gas prior to use. After catalyst addition to the reaction flask, a vacuum is applied to remove volatile olefins that are generated. After ~4 hours reaction time, the vacuum is broken and the metathesized unsaturated polyol ester is cooled to room temperature.

The metathesized canola oil is diluted in hexanes ([110-54-3], EMD, Billerica, Mass.). To the diluted material, 2% bleaching clay (Filtrol F-160, BASF, Florham Park, N.J.) is added and mixed for ~6 hours. The oil is filtered through a bed of Celite® 545 diatomaceous earth. The oil is treated a second time with 2% bleaching clay (Filtrol F-160, BASF, Florham Park, N.J.) for ~6 hours. The oil is filtered through a bed of Celite® 545 diatomaceous earth and then rotary evaporated to concentrate.

The remetathesized canola oil is then passed through a wipe film evaporator at 180° C. and <0.5 Torr vacuum to remove olefins up to and including C-18 chain lengths. A representative example is summarized in the table below.

| Example | Oil Blend (g) | Catalyst[a] (g) | Max Temperature (° C.) | Max Vacuum (Torr) |
|---|---|---|---|---|
| 2 | 500 | 0.27 | 65 | 0.2 |

[a]Tricyclohexylphosphine [4,5-dimethyl-1,3-bis(2,4,6-trimethylphenyl)imidazol-2-ylidene] [2-thienylmethylene]ruthenium (II) dichloride [1190427-50-9] available as CatMETium RF-3 from Evonik Corporation, Parsippany, NJ.

The sample 2 is analyzed for weight average molecular weight, iodine value, free hydrocarbon content and oligomer index, using methods described previously, and is found to approximately have the following values:

| Example | Mw (g/mol) | Iodine Value (cg/g) | Free Hydrocarbon content (wt %) | Oligomer Index |
|---|---|---|---|---|
| 2 | 13,000 | 80 | 0.5 | 0.07 |

Example 3: Synthesis of Metathesized Unsaturated Polyol Esters

Prior to the metathesis reaction, the RBD (refined, bleached, and deodorized) oil is pre-treated by mixing the oil with 2% (by weight) bleaching clay (Filtrol F-160, BASF, Florham Park, N.J.) and heating to 120° C. with a nitrogen sweep for 1.5 hours. The oil is cooled to room temperature, filtered through a bed of Celite® 545 diatomaceous earth (EMD, Billerica, Mass.), and stored under inert gas until ready to use.

To a round-bottomed flask, the oil is added and sub-surface sparged with inert gas while mixing and heating to 55° C. The catalyst is dissolved in 1,2-dichloroethane ([107-06-2], EMD, Billerica, Mass.) that is stored over 4 Å molecular sieves and sub-surface sparged with inert gas prior to use. After catalyst addition to the reaction flask, a vacuum is applied to remove volatile olefins that are generated. After ~4 hours reaction time, the vacuum is broken and the metathesized unsaturated polyol ester is cooled to room temperature.

The metathesized oil is diluted in hexanes ([110-54-3], EMD, Billerica, Mass.). To the diluted material, 2% bleaching clay (Filtrol F-160, BASF, Florham Park, N.J.) is added and mixed for ~6 hours. The metathesized oil is filtered through a bed of Celite® 545 diatomaceous earth. The metathesized oil is treated a second time with 2% bleaching clay (Filtrol F-160, BASF, Florham Park, N.J.) for ~6 hours. The metathesized oil is filtered through a bed of Celite® 545 diatomaceous earth and then rotary evaporated to concentrate.

The metathesized unsaturated polyol ester is then passed through a wipe film evaporator at 180° C. and <0.5 Torr vacuum to remove olefins up to and including C-18 chain lengths. Representative examples are summarized in the table below.

| Example | Starting unsaturated polyol ester | Pretreated Oil (g) | Catalyst[a] (g) | Max Temperature (° C.) | Max Vacuum (Torr) |
|---|---|---|---|---|---|
| 3A | High erucic acid rapeseed oil | 500 | 0.25 | 61 | 7.9 |
| 3B | Blend of High erucic acid rapeseed oil and canola oil, 50/50 by weight | 500 (250 g HEAR oil and 250 g canola oil) | 0.25 | 61 | 7.9 |
| 3C | High oleic soybean oil | 500 | 0.25 | 61 | 7.9 |

[a]Tricyclohexylphosphine [4,5-dimethyl-1,3-bis(2,4,6-trimethylphenyl)imidazol-2-ylidene] [2-thienylmethylene]ruthenium (II) dichloride [1190427-50-9] available as CatMETium RF-3 from Evonik Corporation, Parsippany, NJ.

Example 4

Hydrogenations are performed in a T316 stainless steel, 600 ml Parr reactor (Model Number 4563) containing internal cooling coils and a stir shaft with 2 impellers comprised of 4 blades each. The metathesized unsaturated polyol ester (approximately 200 g) is dissolved in hexanes (120 ml, [110-54-3], EMD, Billerica Ma). To this solution is added a slurry of Nickel on Silica (20 g, [7440-02-0], Catalog #28-1900, Strem Chemicals, Inc., Newburyport, Mass.). The slurried mixtures is transferred via vacuum to the Parr reactor. The mixture is degassed with several vacuum/nitrogen fill cycles. Then with stirring (800-900 rpm), hydrogen gas (550-650 psig, [1333-74-0], UHP grade, Wright Brothers, Inc., Montgomery, Ohio) is charged to the reactor. The reaction is heated at 150° C. and hydrogen gas pressure reduction monitored until constant (~12 hours).

The reaction is cooled to 60° C. and drained from the reactor. The reactor is rinsed with methyl tert-butyl ether ([1634-04-4], EMD, Billerica, Mass.) and combined with the solid hydrogenated metathesized polyol ester. A hot filtration is then performed to remove the catalyst, followed by vacuum to remove all residual solvent. Fully hydrogenated materials are obtained using the method above. Lower hydrogenation levels are obtained by decreasing the reaction temperature to 125 degrees Celsius using 5 grams of catalyst and reducing the reaction time and hydrogen consumed. Iodine Value (IV) is measured, as described elsewhere.

Example 5

The metathesis monomers, dimers, trimers, tetramers, pentamers, and higher order oligomers from the product in Example 2 are fully separated by SFC using the method described above. The individual SFC fractions are collected and trimers, tetramers, and higher order oligomers are combined. The oligomer index of this sample is about 1.

Examples A-D are examples of liquid compositions comprising a polyol ester that may be used to impregnate a wipe:

Examples A-D

| Component | A | B | C | D |
|---|---|---|---|---|
| Water | Q.S. | Q.S. | Q.S. | Q.S. |
| Metathesized Polyol Ester; from Examples 1-5[1] | 3.9 | 2.0 | 4.4 | 4.9 |
| First Emollient[2] | | 1.1 | | |
| Second Emollient[3] | | | | 0.4 |
| First Emulsier[4] | 1.3 | 1.4 | 1.6 | |
| Second Emulsier[5] | 0.7 | 0.9 | 1.1 | |
| Third Emulsier[6] | | | 0.3 | |
| Fourth Emulsifier[7] | | | | 0.6 |
| First Rheology Modifier[8] | 0.11 | 0.15 | 0.18 | 0.12 |
| pH Buffer System[10] | 1.1 | 1.1 | 1.1 | 1.1 |
| Preservative System[11] | 1.0 | 1.0 | 1.0 | 1.0 |
| Anti-Oxidant[12] | | 0.1 | | |

[1]Metathesized Polyol Esters of the present invention;
[2]High Linoleic Sunflower Seed Oil (NuSun Sunflower Seed Oil from Cargill, Minneapolis, MN)
[3]Microcrystalline Wax or Beeswax or Fatty Alcohols or mixtures thereof (W835 microcrystalline wax from Crompton, Petrolia, PA, Beeswax SP-422P from Strahl & Pitsch, West Babylon, NY, Stearyl Alcohol, Cetyl Alcohol, and Cetearyl Alcohol from Procter & Gamble Chemicals, Cincinnati, OH)
[4]Glyceryl Stearate Citrate (Imwitor 372P from Peter Cremer, Cincinnati, OH)
[5]Sodium Stearate, (OP-100V from Hallstar Inc., Chicago, IL)
[6]Steareth-20 (BRIJ-S20 from Croda Inc, Edison, NJ).
[7]Steareth-2 (BRIJ-S2 from Croda Inc, Edison, NJ)
[8]Xanthan Gum (Jungbunzlauer, Basel, Switzerland)
[9]Fumed Silica or treated fumed silica (M-5 or TS-720 from Cabot, Boston, MA)
[10]pH buffer (mixture of trisodium citrate and citric acid from Jungbunzlauer, Basel, Switzerland)
[11]Mixture of Sodium Benzoate, Disodium EDTA, Benzyl Alcohol, Phenoxyethanol, ethylhexyl glycerin, and water; or mixture of sodium benzoate, disodium EDTA, sorbitan caprylate and water.
[12]Tocopherol (Natural Vitamin E from BASF, Florham Park, NJ)

Examples 6-8

| Lotion Compositions | | |
|---|---|---|
| Ex. | Ingredients | % w/w |
| 6 | Aqua | Q.S. |
| | Disodium EDTA | 0.10 |
| | Sodium Benzoate | 0.18 |
| | Xanthan Gum* | 0.06 |
| | Glyceryl Stearate Citrate | 0.22 |
| | Sodium Stearate | 0.15 |
| | Metathesized Unsaturated Polyol Ester | 0.45 |
| | Preservative Enhancing Agent□ | 0.20 |
| | Citric Acid | 0.53 |
| | Trisodium Citrate | 0.33 |
| | Perfume | 0.07 |
| 7 | Aqua | Q.S. |
| | Disodium EDTA | 0.10 |
| | Sodium Benzoate | 0.24 |
| | Xanthan Gum* | 0.18 |
| | Polyoxyethylene (2) Stearyl Ether | 0.22 |
| | Polyoxyethylene (20) Stearyl Ether | 0.15 |
| | Metathesized Unsaturated Polyol Ester | 0.45 |
| | Preservative Enhancing Agent□ | 0.20 |
| | Citric Acid | 0.53 |
| | Trisodium Citrate | 0.33 |
| | Perfume | 0.14 |
| 8 | Aqua | Q.S. |
| | Disodium EDTA | 0.10 |
| | Sodium Benzoate | 0.18 |
| | Xanthan Gum* | 0.10 |
| | Sorbitan Stearate | 0.28 |
| | Polyoxyethylene (20) sorbitan monostearate | 0.18 |
| | Metathesized Unsaturated Polyol Ester | 0.45 |
| | Preservative Enhancing Agent□ | 0.20 |
| | Citric Acid | 0.53 |
| | Trisodium Citrate | 0.33 |
| | Perfume | 0.14 |

Each of the Examples A-D is made by the following recipe:

1) Weigh out correct amount of water into a clean beaker,
2) While shearing at 4000 to 7000 RPM with a rotor-stator mixer (Silverson's Model #L4RT-A or Ika-Werke's Ultra Turrax T50 Basic or equivalent), add the Disodium ethylenediamine tetraacetic acid, Trisodium Citrate, and Sodium Benzoate. Mix for 3 to 5 minutes.
3) While keeping the rotor-stator on at 4000 to 7000 RPM, slowly add the Xanthan Gum and mix for 10 to 15 minutes,
4) While keeping the rotor-stator mixer on, add the Sodium Stearate and mix until the pH exceeds 8.7. If using Steareth-20 (see example D above) in place of the Sodium Stearate, mix until it is completely dissolved and do not monitor the pH
5) In another clean beaker, weigh together both the Metathesized Polyol Ester and Glyceryl Stearate Citrate and heat to 60 to 80 C. If using both the Steareth-2 and a second emollient like a fatty alcohol (see Example D above) in place of the Glyceryl Stearate Citrate, mix them with the metathesized polyol ester and heat to 60 to 80 C. Mix with a spatula until a homogeneous liquid results. Slowly add the heated liquid mixture of the Metathesized Polyol Ester and dissolved emulsifier(s) into the vortex created by the rotor-stator mixer. Mix for 5 to 10 minutes at 4000 to 7000 RPM with the rotor stator mixer.
6) Add the preservative enhancing agent listed above and continue mixing at 4000 to 7000 RPM. Mix for 1 to 5 minutes.
7) While maintaining mixing at 4000 to 7000 RPM, add enough Citric Acid to reach a pH in the range of 3.7 to 4.1. Mix for an additional 5 to 15 minutes. Turn off mixer and dispense into a clean container.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wet wipe comprising a composition, said composition comprising;
    a) from about 0.1% to about 4% of a metathesized unsaturated polyol ester, by weight of the composition, said metathesized unsaturated polyol ester having the following properties:
        (i) a weight average molecular weight from about 5,000 Daltons to about 50,000 Daltons;
        (ii) an oligomer index from greater than 0 to 1;
        (iii) an iodine value from about 30 to about 200;
    b) from about 0.2% to about 4%, by weight of the composition, of an emollient selected from the group consisting of vegetable oils, hydrogenated vegetable oils, esters, lanolin oil and lanolin wax, hydrophobic emollients, dimethicone fluids, vegetable butters, coconut oil, ethylene vinyl acetate polymers, microcrystalline wax, paraffin wax, beeswax, carnauba wax, ozokerite wax, ceresin wax, alcohols, and mixtures thereof; and
    c) from about 90% to about 98% water, by weight of the composition; and
    wherein the metathesized unsaturated polyol ester is hydrogenated.

2. A wet wipe according to claim 1, wherein said metathesized unsaturated polyol ester has a weight average molecular weight from about 6,000 Daltons to about 30,000 Daltons.

3. A wet wipe according to claim 1 wherein said metathesized unsaturated polyol ester has an iodine value from about 30 to about 150.

4. A wet wipe comprising a composition, said composition comprising:
    a) from about 0.1% to about 4% of a metathesized unsaturated polyol ester, by weight of the composition, said metathesized unsaturated polyol ester having a weight average molecular weight of from about 5,000 Daltons to about 50,000 Daltons; and two or more of the following properties:
        (i) a free hydrocarbon content, based on total weight of metathesized unsaturated polyol ester of from about 0% to about 5%;
        (ii) an oligomer index from greater than 0 to 1;
        (iii) an iodine value of from about 8 to about 200; and
    b) from about 0.2% to about 4%, by weight of the composition, of an emollient selected from the group consisting of vegetable oils, hydrogenated vegetable oils, esters, lanolin oil and lanolin wax, hydrophobic emollients, dimethicone fluids, vegetable butters, coconut oil, ethylene vinyl acetate polymers, microcrystalline wax, paraffin wax, beeswax, carnauba wax, ozokerite wax, ceresin wax, alcohols, and mixtures thereof; and
    c) from about 90% to about 98% water, by weight of the composition; and
    wherein the metathesized unsaturated polyol ester is hydrogenated.

5. A wet wipe according to claim 4, wherein said metathesized unsaturated polyol ester has an iodine value of from about 10 to about 200.

6. A wet wipe according to claim 4, wherein said metathesized unsaturated polyol ester has an oligomer index from about 0.001 to 1.

7. The wet wipes composition according to claim 4, wherein at least one emulsifier is nonionic.

8. The wet wipes composition according to claim 4, wherein the one or more metathesized unsaturated polyol ester oligomers are self-metathesized.

9. The wet wipes composition according to claim 4, wherein the one or more metathesized unsaturated polyol ester oligomers are cross-metathesized.

10. The wet wipes composition according to claim 4, wherein the lotion loading is from about 200% to about 600% by weight of the substrate.

11. A wet wipe comprising a fibrous co-formed structure, and further comprising the wet wipes composition according to claim 4.

12. The wipe according to claim 4, wherein the wet wipe composition further comprises from about 0.01% to about 3% of an antioxidant.

13. The wipe composition of claim 4, wherein the wipe composition further comprises one or more additional benefit agents selected from the group consisting of anti-rash agents, vitamins, chelants, enzymes, enzyme inhibitors, sensates, anti-bacterial agents, moisturizers, anti-eczema agents, anti-erythema agents, anti-itch agents, anti-hemorrhoid agents, anti-odor agents, and mixtures thereof.

* * * * *